(12) United States Patent
Liu et al.

(10) Patent No.: US 6,574,520 B1
(45) Date of Patent: Jun. 3, 2003

(54) FLEXIBLE MANUFACTURING SYSTEM

(75) Inventors: le;.5qVincent B. Liu, Cincinnati, OH (US); Donald L. Wires, Loveland, OH (US); Michael J. Lamping, Cincinnati, OH (US); Albert M. Fischer, Fairfield, OH (US); Gary L. Miller, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/496,480

(22) Filed: Feb. 2, 2000

(51) Int. Cl.$^7$ .............................................. G06F 19/00
(52) U.S. Cl. ...................... 700/96; 700/117; 700/128; 29/563; 29/564; 493/478
(58) Field of Search .............................. 700/95, 96, 97, 700/105, 117, 122, 128, 127; 29/563, 564, 700, 701; 493/477, 478; 198/860.1, 860.2

(56) References Cited

U.S. PATENT DOCUMENTS

| | | | |
|---|---|---|---|
| 3,860,003 A | 1/1975 | Buell | |
| 4,218,815 A | 8/1980 | Cumming | 29/563 |
| 4,381,781 A | 5/1983 | Sciaraffa et al. | |
| 4,472,783 A | * 9/1984 | Johnstone et al. | 700/182 |
| 4,492,297 A | 1/1985 | Sticht | 198/345.3 |
| 4,789,039 A | * 12/1988 | Bjork | 180/124 |
| 4,807,420 A | 2/1989 | Barker | 53/51 |
| 4,857,067 A | 8/1989 | Wood et al. | |
| 4,938,753 A | 7/1990 | Van Gompel et al. | |
| 5,062,195 A | 11/1991 | Binder | 483/15 |
| 5,083,364 A | 1/1992 | Olbrich et al. | 29/564 |
| 5,151,092 A | 9/1992 | Buell et al. | |
| 5,155,679 A | * 10/1992 | Jain et al. | 700/106 |
| 5,212,645 A | * 5/1993 | Wildes et al. | 700/108 |
| 5,221,274 A | 6/1993 | Buell et al. | |
| 5,353,490 A | 10/1994 | Kukuljan | 29/564 |
| 5,361,486 A | 11/1994 | Harmsen et al. | 29/563 |
| 5,383,988 A | 1/1995 | Herrmann et al. | 156/64 |
| 5,492,591 A | 2/1996 | Herrmann et al. | 156/538 |
| 5,518,801 A | 5/1996 | Chappell et al. | |
| 5,539,975 A | 7/1996 | Kukuljan et al. | 29/701 |
| 5,554,145 A | 9/1996 | Roe et al. | |
| 5,569,234 A | 10/1996 | Buell et al. | |
| 5,580,411 A | 12/1996 | Nease et al. | |
| 5,615,468 A | 4/1997 | Chubbuck | 29/38 C |
| 5,657,529 A | 8/1997 | Bohn et al. | 29/563 |
| 5,669,897 A | 9/1997 | Lavon et al. | |
| 5,868,899 A | 2/1999 | Gundersen | 156/538 |
| 5,914,880 A | * 6/1999 | Yasojima et al. | 700/159 |
| 6,004,306 A | 12/1999 | Robles et al. | |
| 6,185,469 B1 | * 2/2001 | Lewis et al. | 700/99 |
| 6,349,237 B1 | * 2/2002 | Koren et al. | 700/96 |

FOREIGN PATENT DOCUMENTS

| | | |
|---|---|---|
| EP | 0267861 A2 | 5/1988 |
| EP | 0 589 859 A | 3/1994 |
| WO | WO 95/13775 A1 | 5/1995 |
| WO | WO95/32694 | 12/1995 |
| WO | WO95/32695 | 12/1995 |
| WO | WO95/32696 | 12/1995 |

OTHER PUBLICATIONS

AeroGo, Inc. Sales brochure for GAPMASTER™ Aero-Caster (GM 4/96).

* cited by examiner

Primary Examiner—Leo Picard
Assistant Examiner—Paul Rodriguez
(74) Attorney, Agent, or Firm—Michael S. Kolodesh; Jay A. Krebs; Ken K. Patel

(57) ABSTRACT

A flexible manufacturing system including at least one module, a operational unit mounted to said at least one module and a local controller operatively connected to the operational unit. The local controller is adapted to control the operational unit. The at least one module and the local controller together are capable of operating in a standalone operation or of integration into a flexible manufacturing system. The local controller is further adapted to receive a reference signal from the flexible manufacturing system and to synchronize the operational unit to the flexible manufacturing system when the at least one module is connected to the flexible manufacturing line.

7 Claims, 29 Drawing Sheets

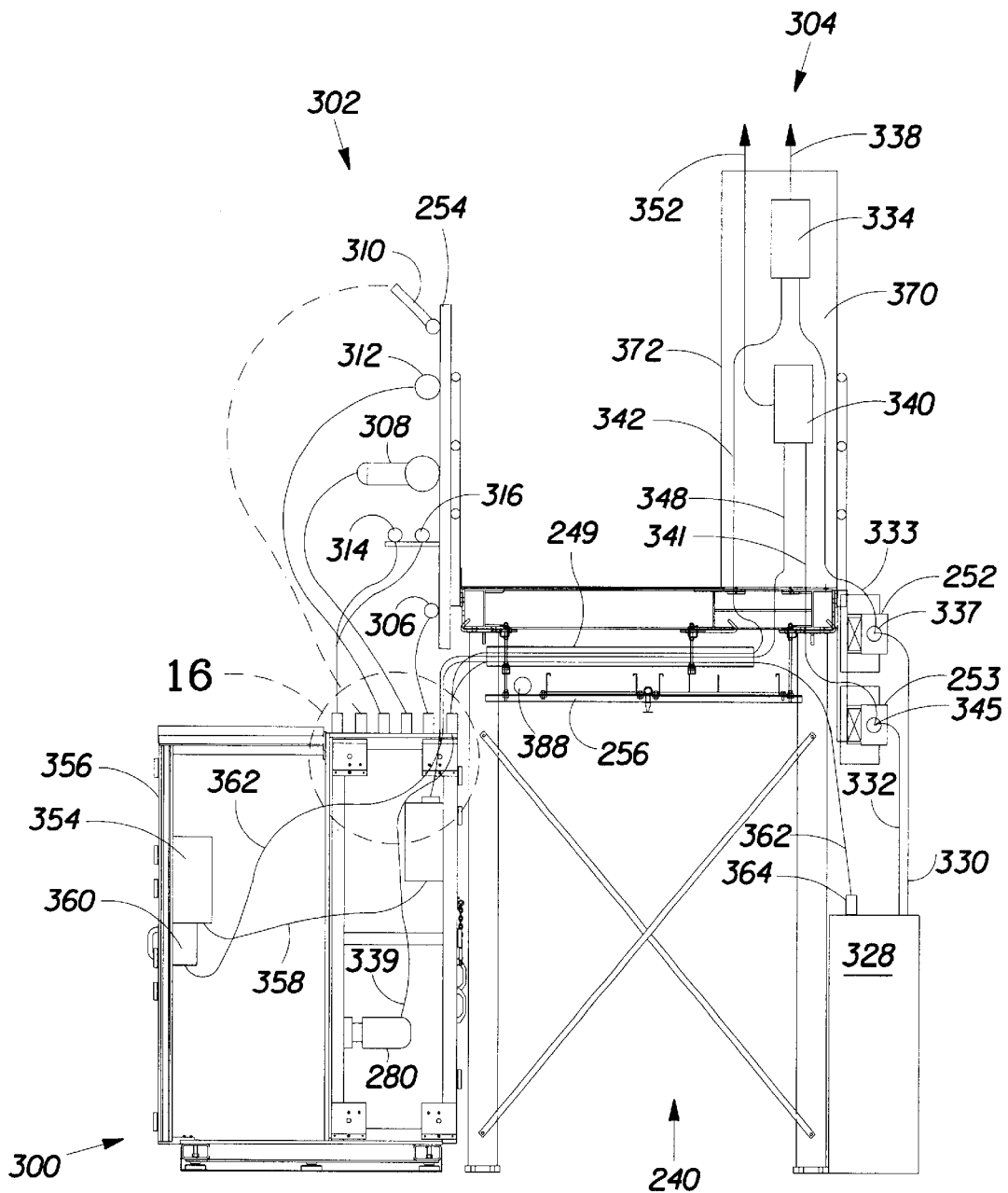
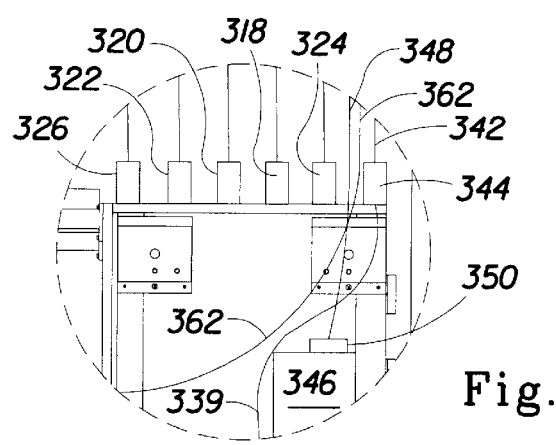
Fig. 15
Fig. 16

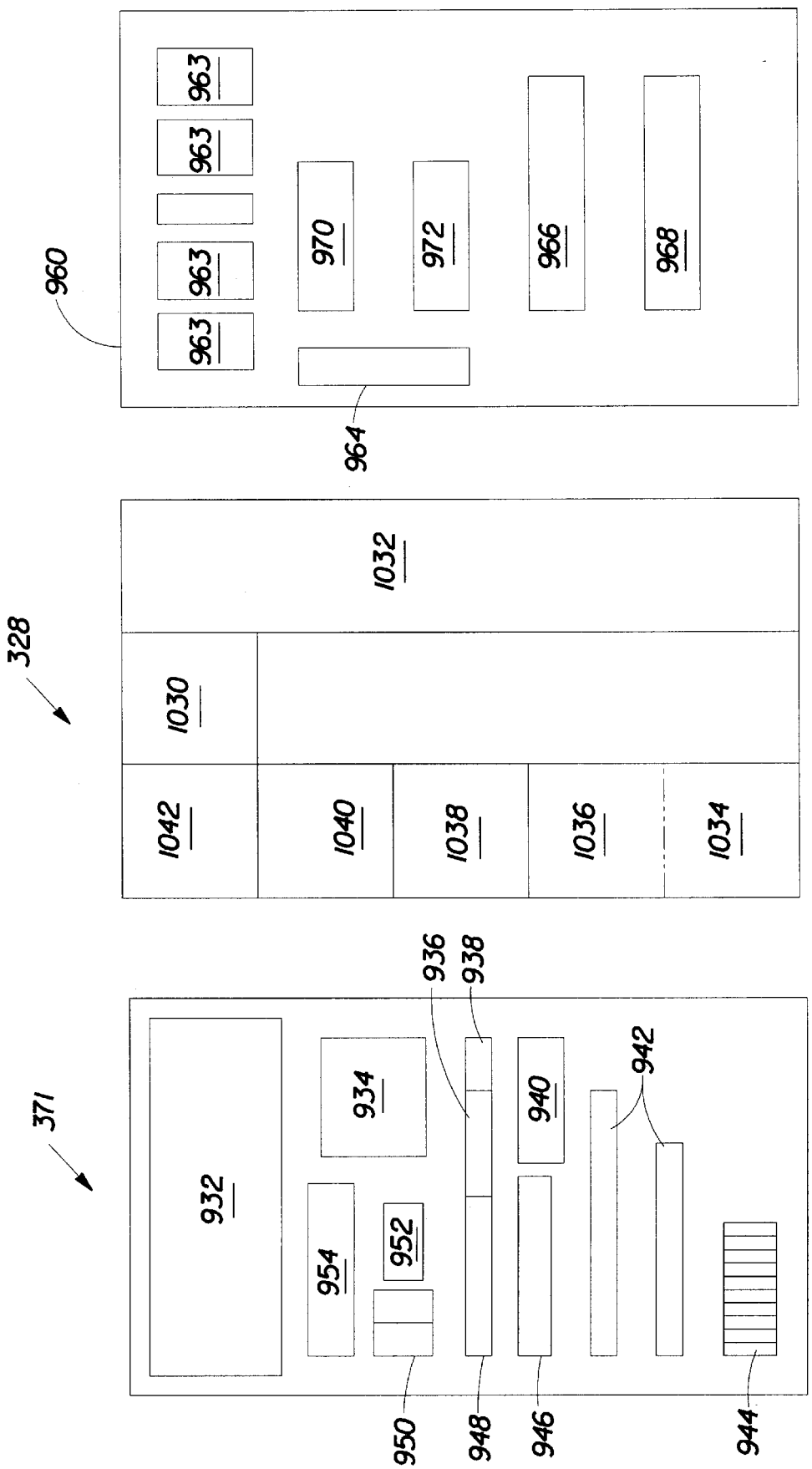

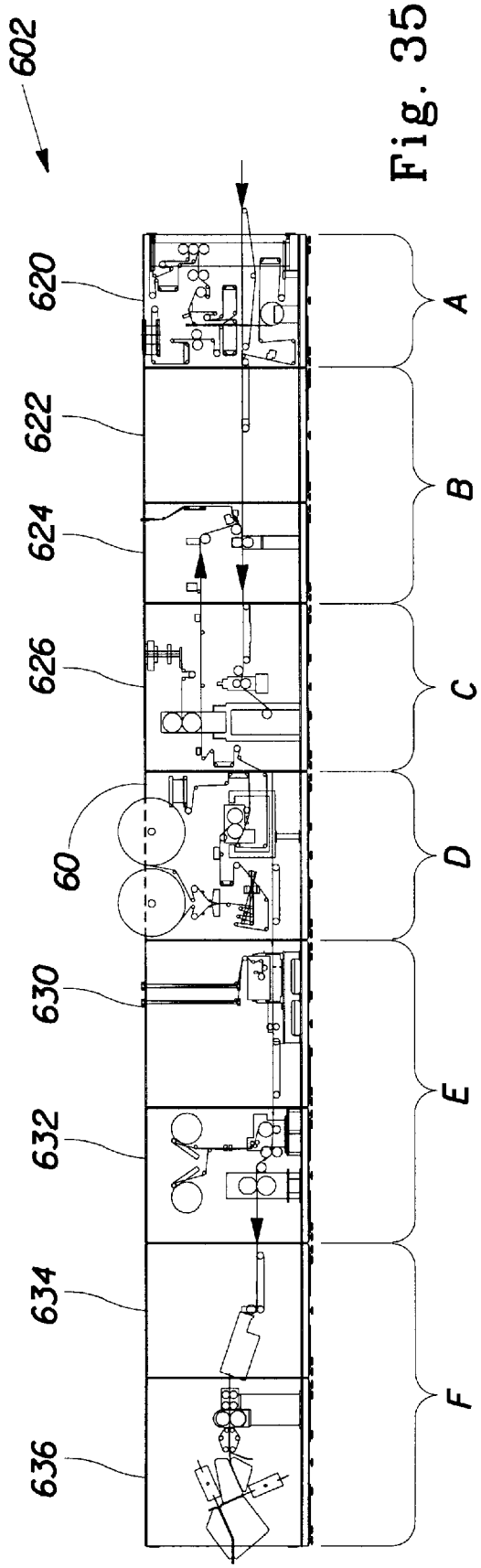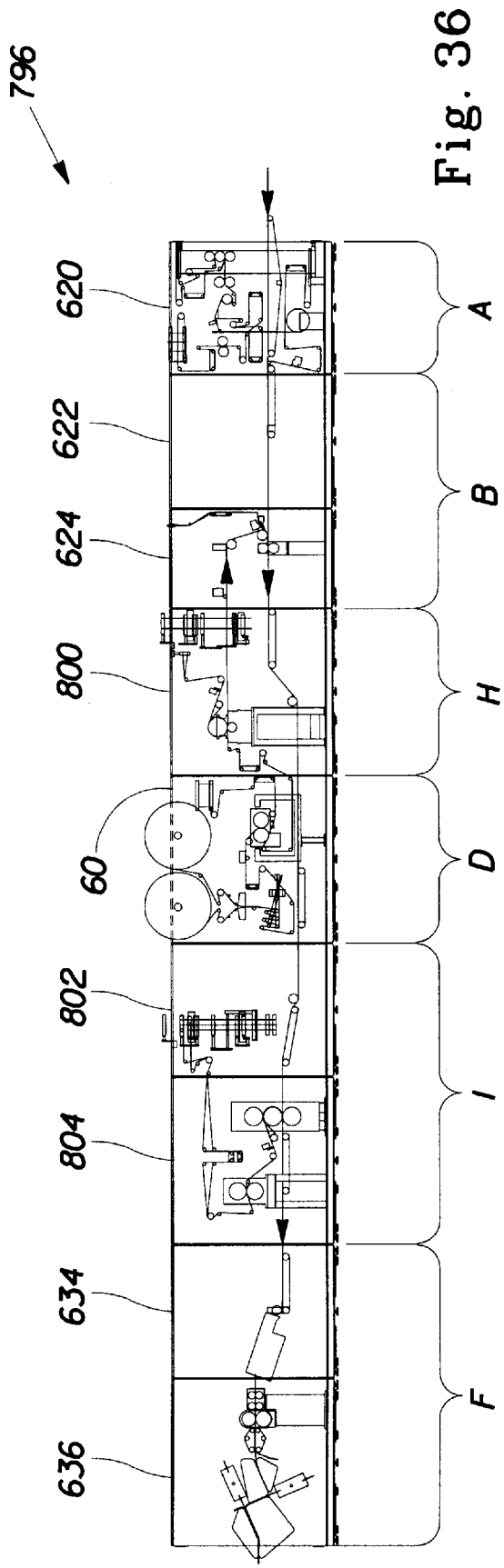

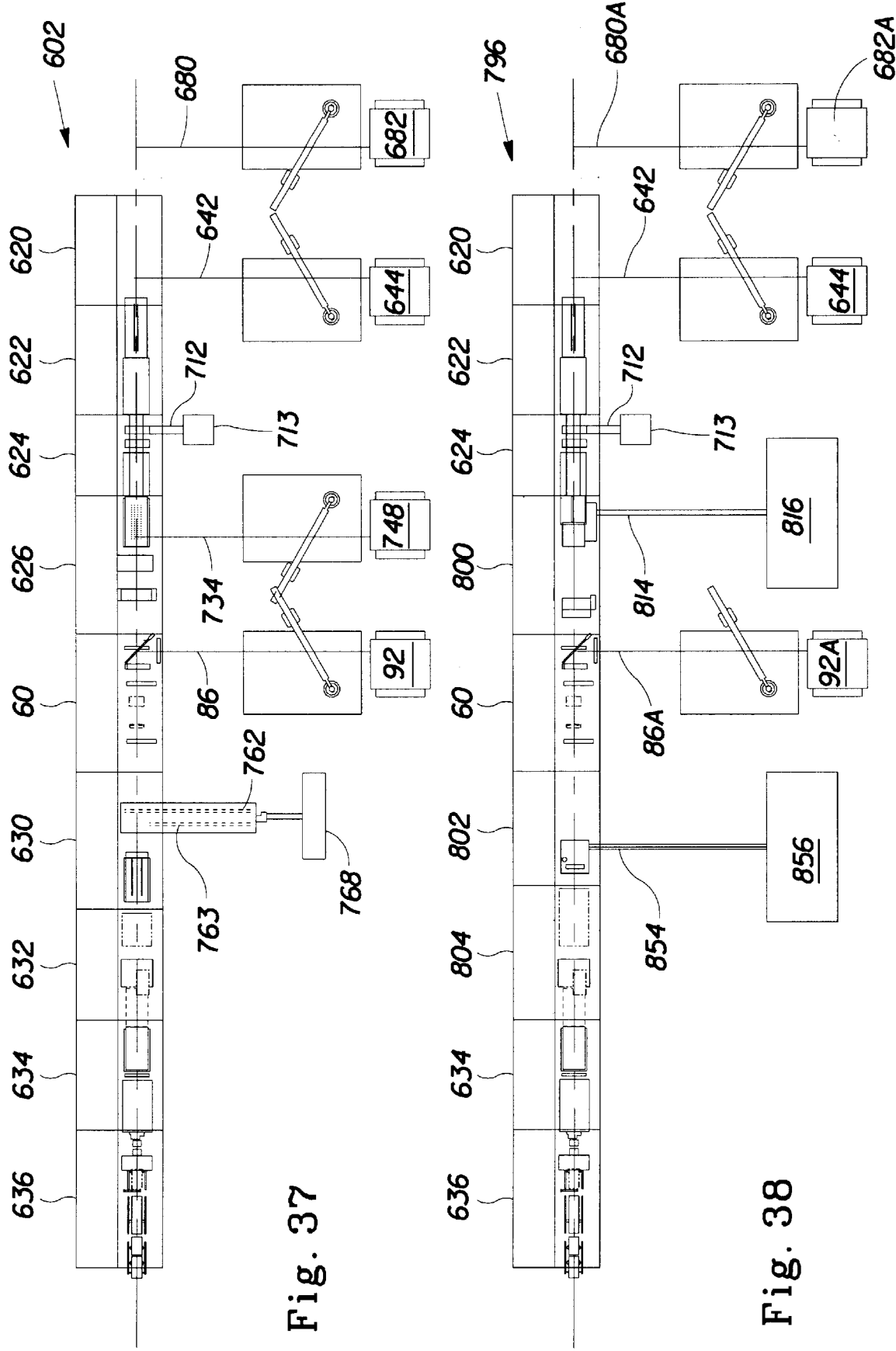

FLEXIBLE MANUFACTURING SYSTEM

FIELD OF THE INVENTION

This invention relates to a flexible manufacturing system. More particularly, this invention relates to a flexible manufacturing system that allows for efficient product development and line changes to accommodate changes in product design.

BACKGROUND OF THE INVENTION

Disposable, reusable and durable products such as diapers, adult incontinence articles, feminine hygiene tampons, sanitary napkins, underpants, shirts, shorts, swimsuits, gowns, pants, coats, gloves, scarves, surgical drapes, bibs, blankets, sheets, pillow cases, etc. may be manufactured on high speed converting lines. A converting line utilizes a web-based carrier to which many source materials, whether in a continuous web or discrete pieces, are processed and/or attached to the web to create a finished product.

Although a converting line may allow for high speed production, typical converting lines are inflexible in that line changes are time consuming and expensive. Product development and implementation of product upgrades usually require extensive testing and construction efforts. A product upgrade may, for example, require the following steps: constructing manual or handmade products incorporating the upgrade in order to test the concept and determine consumer acceptance of such an upgrade; constructing a machine production unit that may manufacture the product upgrade and/or the entire product incorporating the upgrade in order to determine product and process feasibility; constructing a high speed test stand that may manufacture the product upgrade in isolation at high speeds in order to test the feasibility of high speed manufacturing; constructing a prototype line that is able to make complete prototype products at high speeds; reconstructing a high speed production line to implement the process changes necessary for the product upgrade; and testing and debugging the production line. These efforts may be expensive and time consuming, especially when the reconstruction, testing and debugging steps lead to down time of a high speed production line. Then, when a product upgrade is rolled out on multiple production lines, the time and money required to implement even a small change in each individual line may increase dramatically. Often, the time and money required will be prohibitive, and highly desirable product upgrades may be delayed or even eliminated.

Attempts to increase the flexibility of a converting line have been made. U.S. Pat. No. 5,383,988 entitled "Modular Apparatus for Fabricating an Absorbent Article," issued to Thomas R. Herrmann et al. on Jan. 24, 1995 and U.S. Pat. No. 5,492,591 entitled "Modular Apparatus for Fabricating an Absorbent Article," issued to Thomas R. Herrmann et al. on Feb. 20, 1996, for example, describe a system for fabricating absorbent articles that includes a linear array of substantially identical frame modules joined together. A plurality of substantially identical, removable panels that support working devices are mounted to one face of the modules. The Herrmann references describe that mounting the working devices to the removable panels facilitates rapid installation, servicing, adjustment of the working devices and accommodates convenient observation of the operation of such devices.

Another attempt to increase the flexibility of a converting line is disclosed in U.S. Pat. No. 5,868,899 entitled "Process Line for the Production of Absorbent Disposable Products," issued to Dag H. Gundersen on Feb. 9, 1999, which describes a converting line for manufacturing disposable absorbent articles in which removable rectangular carrier plates that carry working devices are attached to vertical and horizontal posts. The posts are arranged sequentially in a framework on the same side of and parallel to a conveyor path movement. The Gundersen reference describes that the working devices in the converting line may be removed from, replaced or inserted into the converting line by removing, replacing or inserting the carrier plate to or from the framework of vertical and horizontal posts.

Although these efforts may allow for quicker physical construction or reconstruction of a converting line once the process for manufacturing a newly developed product has been developed off-line, the steps of constructing a machine production unit that may manufacture the product upgrade and/or the entire product incorporating the upgrade in order to determine product and process feasibility; constructing a high speed test stand that may manufacture the product upgrade in isolation at high speeds in order to test the feasibility of high speed manufacturing; and constructing a prototype line that is able to make complete prototype products at high speeds are still required. Also, the lines disclosed in the Herrmann and Gundersen references, once constructed, still require significant testing and debugging time before the line may be used for production of products. Thus, a method allowing for quicker product and process development is desired. Minimizing down time due to testing and debugging a production converting line after construction or reconstruction is also desirable.

SUMMARY OF THE INVENTION

The present invention comprises a flexible manufacturing system that allows for rapid product and process development and rapid construction or modification of a converting line that implements the new product and process development. The flexible manufacturing system of the present invention includes one or more modules and one or more local controllers. The one or more modules may be operated off-line in a standalone mode for product development and may also be inserted into a prototype line and/or an actual production line. The one or more modules may include one or more operational units. The one or more local controllers may be connected to the one or more modules in order to control the one or more operational units in a standalone mode. In the standalone mode, the one or more modules may be run as a test stand, and the one or more operational units and/or the one or more local controllers may be tested, adjusted or modified off-line of the flexible manufacturing system. Once a process for manufacturing a product upgrade including a portion of the new product has been developed and tested off-line, the one or more modules that include the operational units that will produce that portion of the new product may be inserted into the overall flexible manufacturing system, or one or more modules already in the converting line may be replaced with the module or modules that include the operational units that will produce that portion of the new product. The one or more local controllers may also utilize a reference signal to synchronize the operation of the one or more operational units of the one or more modules when the one or more modules are connected to the overall flexible manufacturing system.

BRIEF DESCRIPTION OF THE DRAWINGS

While the specification concludes with claims particularly pointing out and distinctly claiming the subject matter which is regarded as the present invention, it is believed that the invention will be better understood from the following drawings, in which:

FIG. 15 is a simplified side view of a module connected to electric power and fluid utilities.

FIG. 16 is an enlarged view of an area 23B shown in FIG. 15.

FIG. 27 is an example of one embodiment of a standard main control panel.

FIG. 28 is an example of one embodiment of a power distribution center.

FIG. 29 is an example of one embodiment of a standard adhesive panel.

FIG. 35 is a simplified front view from the operator side of a modular converting operation which in conjunction with the core making operation shown in FIG. 34 could be used to manufacture the diaper shown in FIG. 32.

FIG. 36 is a modified modular converting operation shown in FIG. 35 which in conjunction with the core making operation shown in FIG. 34 could be used to manufacture the diaper shown in FIG. 33.

FIG. 37 is a simplified top view of the modular converting operation shown in FIG. 35.

FIG. 38 is a simplified top view of the modular converting operation shown in FIG. 36.

DETAILED DESCRIPTION OF THE INVENTION

The present invention is directed to a flexible manufacturing system for manufacturing disposable and durable products such as diapers, adult incontinence articles, feminine hygiene tampons, sanitary napkins, clothing, etc. The flexible manufacturing system of the present invention may include one or more modules that may be operated in a standalone mode and that may be operated within the overall flexible manufacturing system. The flexible manufacturing system may also include a control system that controls the one or more modules in a standalone mode and that allows for the one or more modules to be operated as an integral part of the flexible manufacturing system by synchronizing the one or more modules to the rest of the flexible manufacturing system.

Modules

Figure 1:
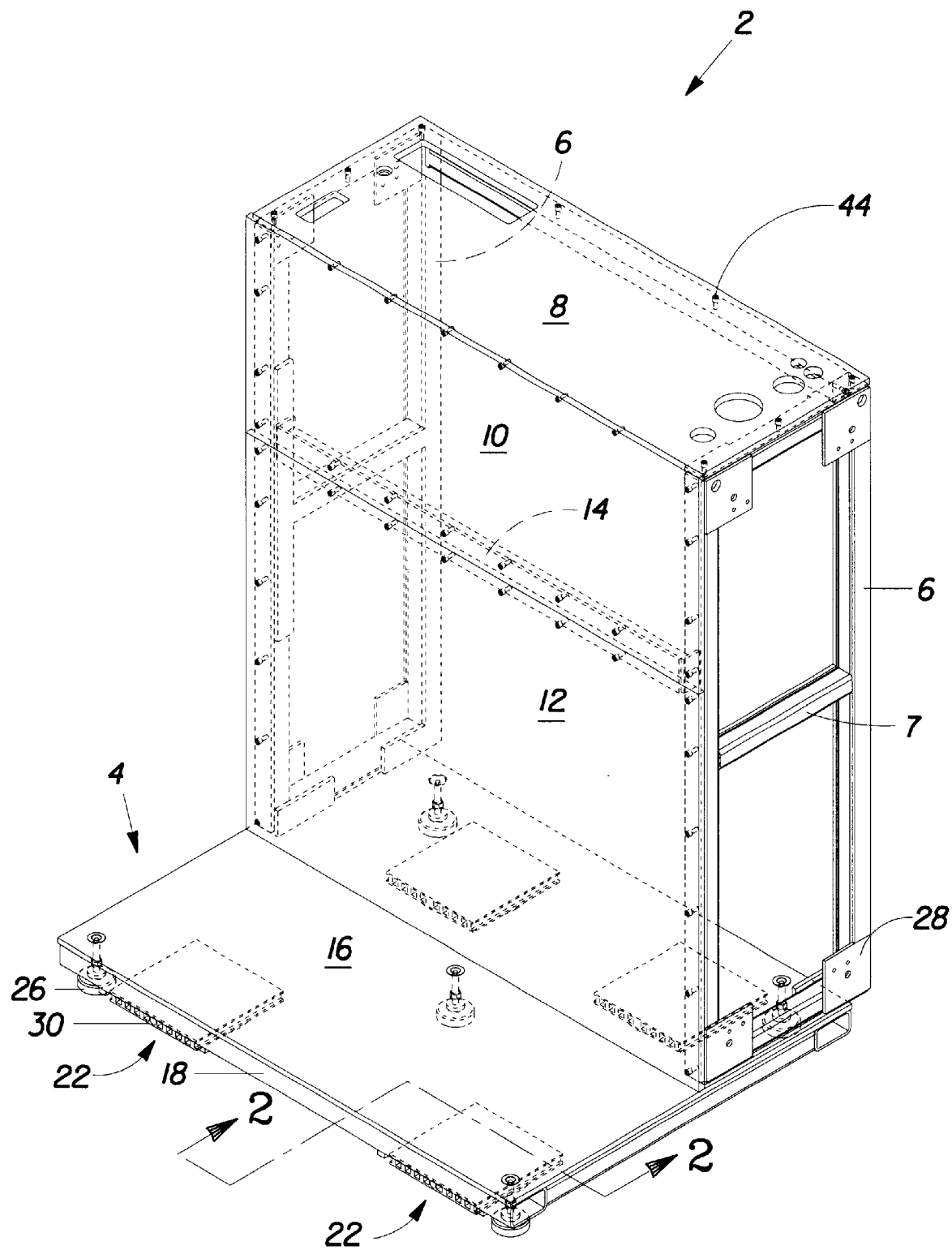
FIG. 1 is a simplified perspective view of a frame construction of a module of the present invention.
Figure 2:
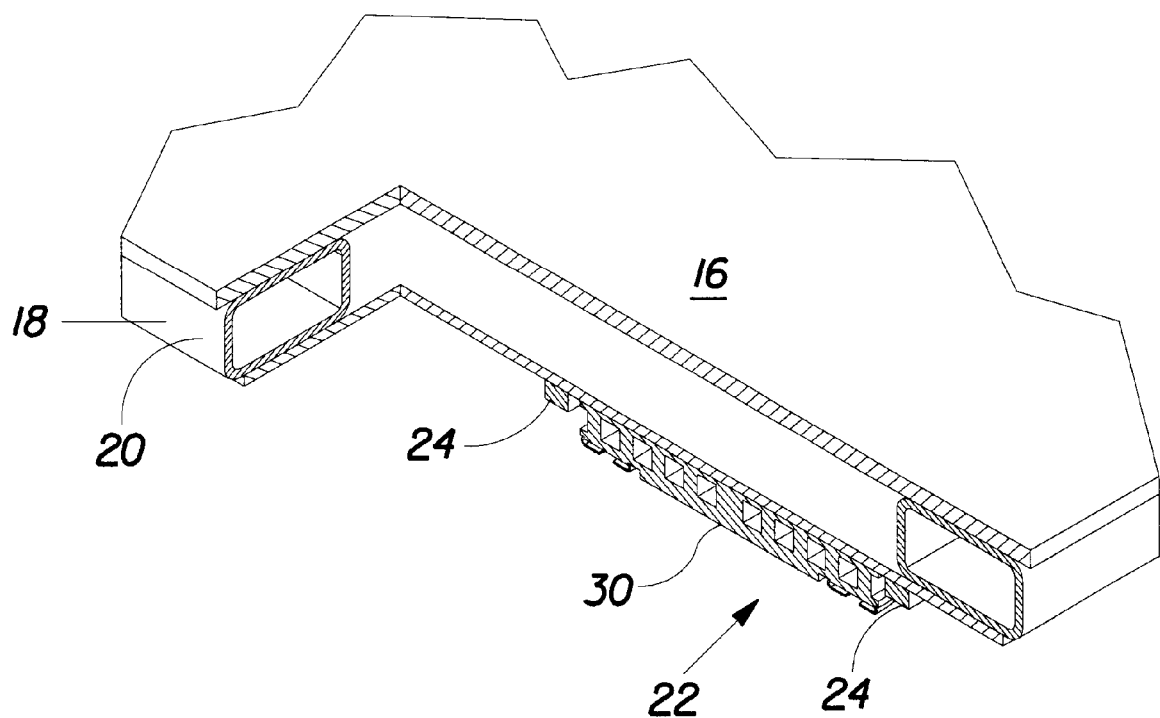
FIG. 2 is an enlarged cutaway view of a base of the module frame shown in FIG. 1.
Figure 12:
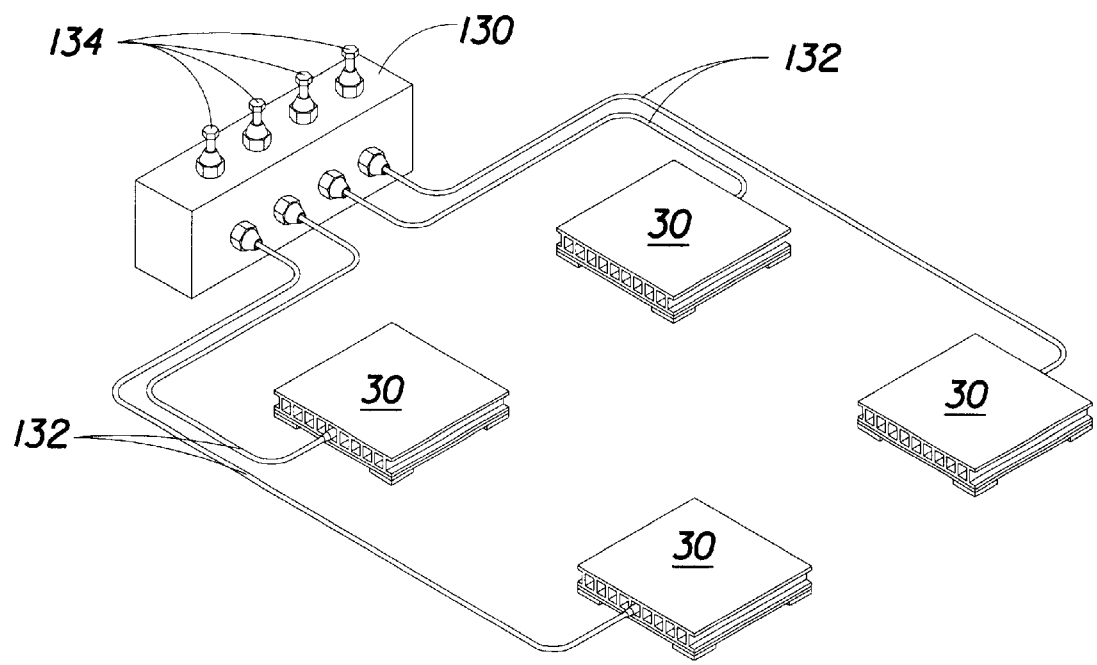
FIG. 12 is a simplified view of a manifold connected to four lifting mechanisms via compressed air lines.

FIGS. 1 and 2, for example, show one embodiment of a module frame 2. The module frame 2 may include a base 4 having a horizontal plate 16 and a perimeterically welded bottom frame 18 formed from a rectangular tube 20. The horizontal plate 16 may be joined to the bottom 18 by welding, bolts, screws, pins or any other means used in the art. The top of the horizontal plate 16 may be connected to two side supports 6 by welding, bolts, screws, pins, etc. The two side supports 6 may be positioned vertically on opposite sides of the horizontal plate 16 and are generally perpendicular to the machine direction. (The term "machine direction" refers to the general direction in which the materials being processed move.) Each side support 6 may form a welded parallelepiped construction having a cross bar 7 and four side plates 28 at the four corners of the side support 6. The two side supports 6 may be connected by a top plate 8 and two vertical plates 10 and 12 such as by using screws 44. For added strength, the vertical plates 10 and 12 may be connected to a cross support 14 which also connects the two side supports 6. The vertical plates 10 and 12 may be of equal size or may be different sizes to accommodate different size operational units. Additionally, the module frame 2 may include one, two, three or more vertical plates such as the vertical plates 10 and 12 shown in FIGS. 1 and 3. The bottom of the horizontal plate 16 may be divided into four regions 22 such as by welded strips 24 for positioning a lifting mechanism 30 (described in more detail below) in each region 22. The module frame 2 may include various numbers of regions 22 and/or numbers of lifting mechanisms 30 depending upon the weight and distribution of the module load and the lifting capability of the lifting mechanisms 30. The lifting mechanisms 30 located under the base 4 may be inflated simultaneously in order to avoid unnecessary tilting of the module and its load. For this, a manifold 130 such as shown in FIG. 12 may distribute air among the lifting mechanisms via compressed air lines 132 connected between the manifold 130 and the lifting mechanisms 30 by adjusting valves 134. Further, the base 4 may include feet 26. In one embodiment, the feet 26 may be individually adjustable in order to level the module 2 and align the module to the rest of the converting line. The module frames may be uniform dimensions or may vary in size. In one embodiment, the width (dimension in the machine direction) may vary, for example, from about 1 meter to about 3 meters to allow for relatively easy handling of the module frame 2. In a particular embodiment, the width of the module frames 2 may be standard dimensions such as about 1 meter, about 1.5 meters, about 2 meters, about 2.5 meters, and/or about 3 meters in order to provide standard modules that may be used to house various sizes and numbers of operational units, and that may limit the number of modules that need to be kept in an inventory to allow for exchange of any module in the converting line. In yet another embodiment, the width of the module frames 2 may all be substantially the same size in order to reduce the inventory required even further.

Figure 7:
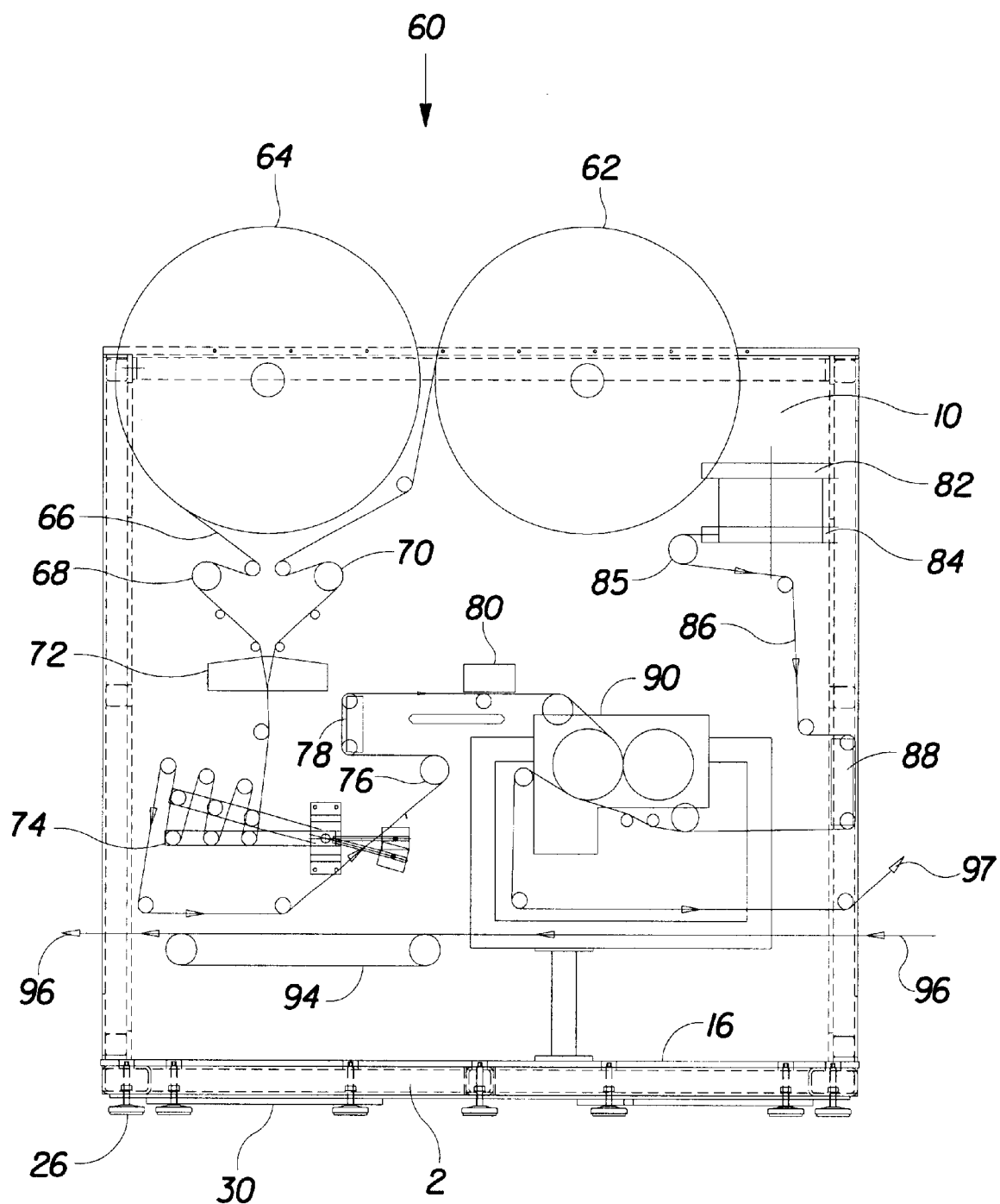
FIG. 7 is a simplified front view from an operator side of one of the modules of the present invention including operational units.

The term "module" refers to a single and physically independent container that may contain one or more operational units to allow the one or more operational units to be moved within a flexible manufacturing system of the present invention. An "operational unit" includes one or more pieces of equipment that may add something to, remove something from, modify, or guide or transport a source material, a web, a product, an element or a component of a product. The term "source material," as used in this application, includes any material supplied to the production machine regardless of the form in which it is supplied, e.g., a single layer or a multiple-layer laminate; a continuous web or discrete pieces; in a roll or in a box, etc., for the purpose of fabricating a product or part of a product. An operational unit, for example, may include a pair of nip rolls, an adhesive applicator, an omega roll, an initial knife, a conveyor, etc. The one or more operational units function inside the module such as by manipulating, transforming or temporarily changing a source material in a designed sequence of a manufacturing process. Some of the operational units, such as heavier ones, may be attached to the horizontal plate 16 or to both the horizontal plate 16 and one or more of the vertical plates 10 and/or 12. Cutting device 90, for example, is shown in FIGS. 7 and 8 connected to both the horizontal plate 16 and the vertical plate 12.

Figure 8:
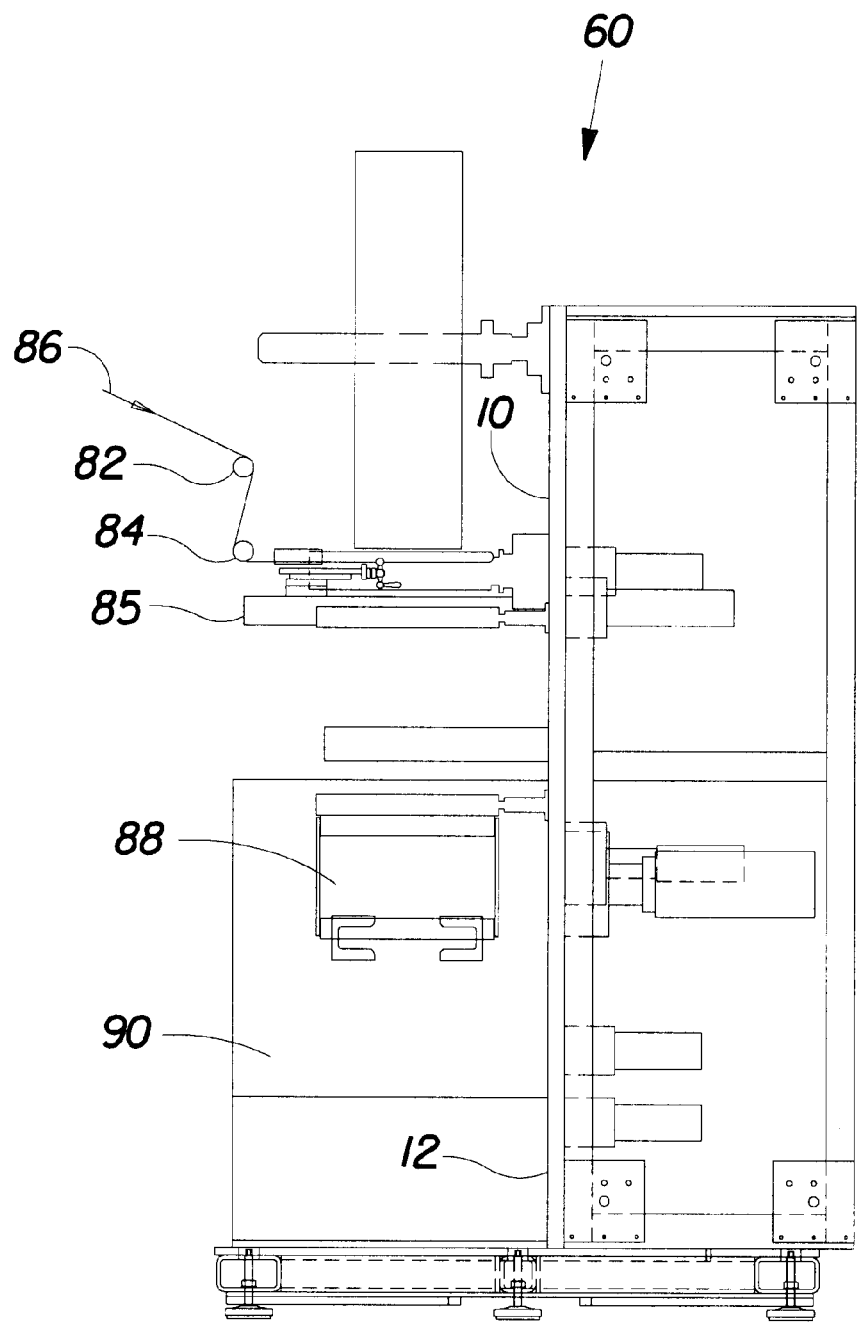
FIG. 8 is a simplified side view of the module shown in FIG. 7.
Figure 9:
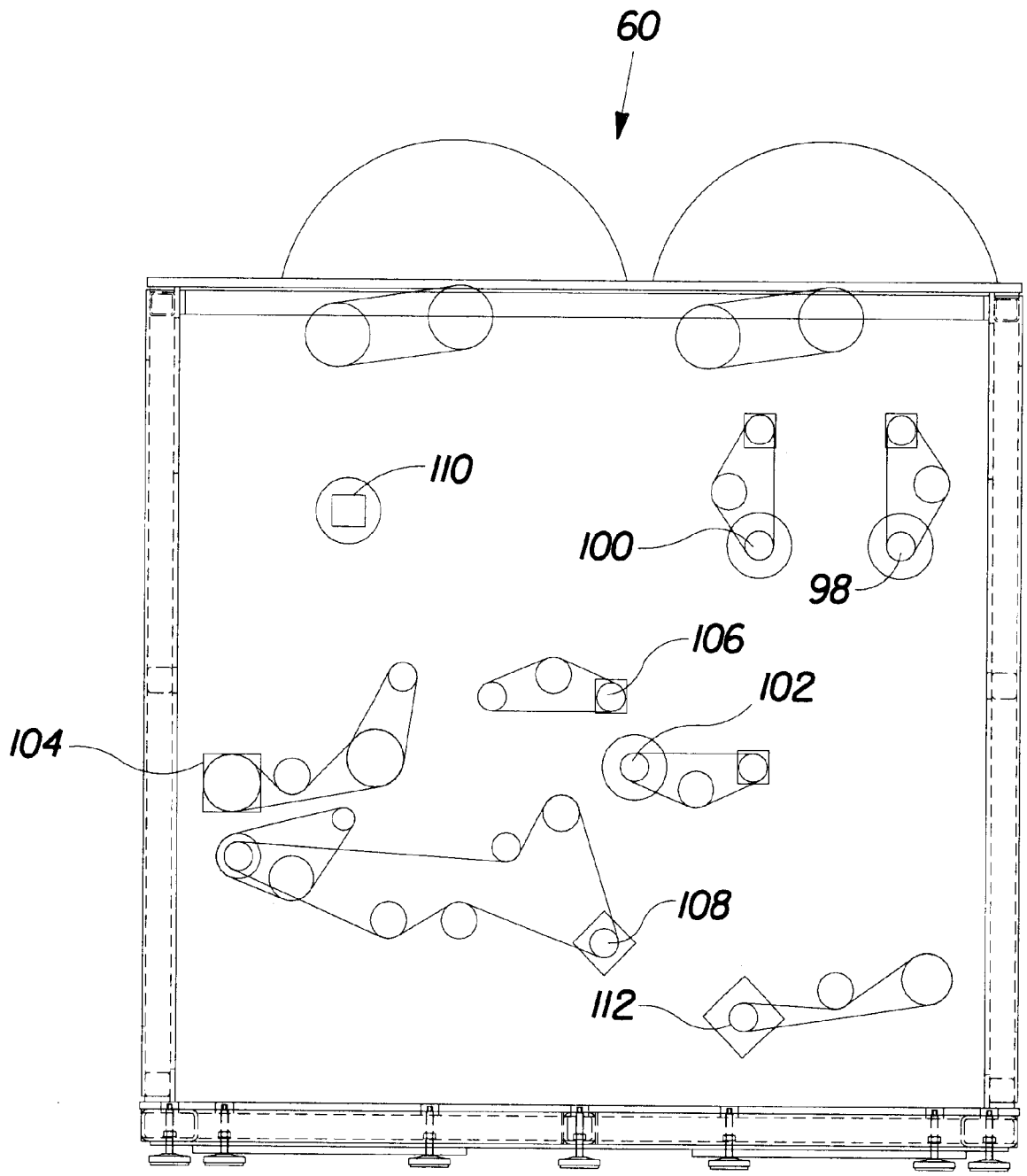
FIG. 9 is a simplified back view from the drive side of the module shown in FIGS. 7 and 8.
Figure 10:
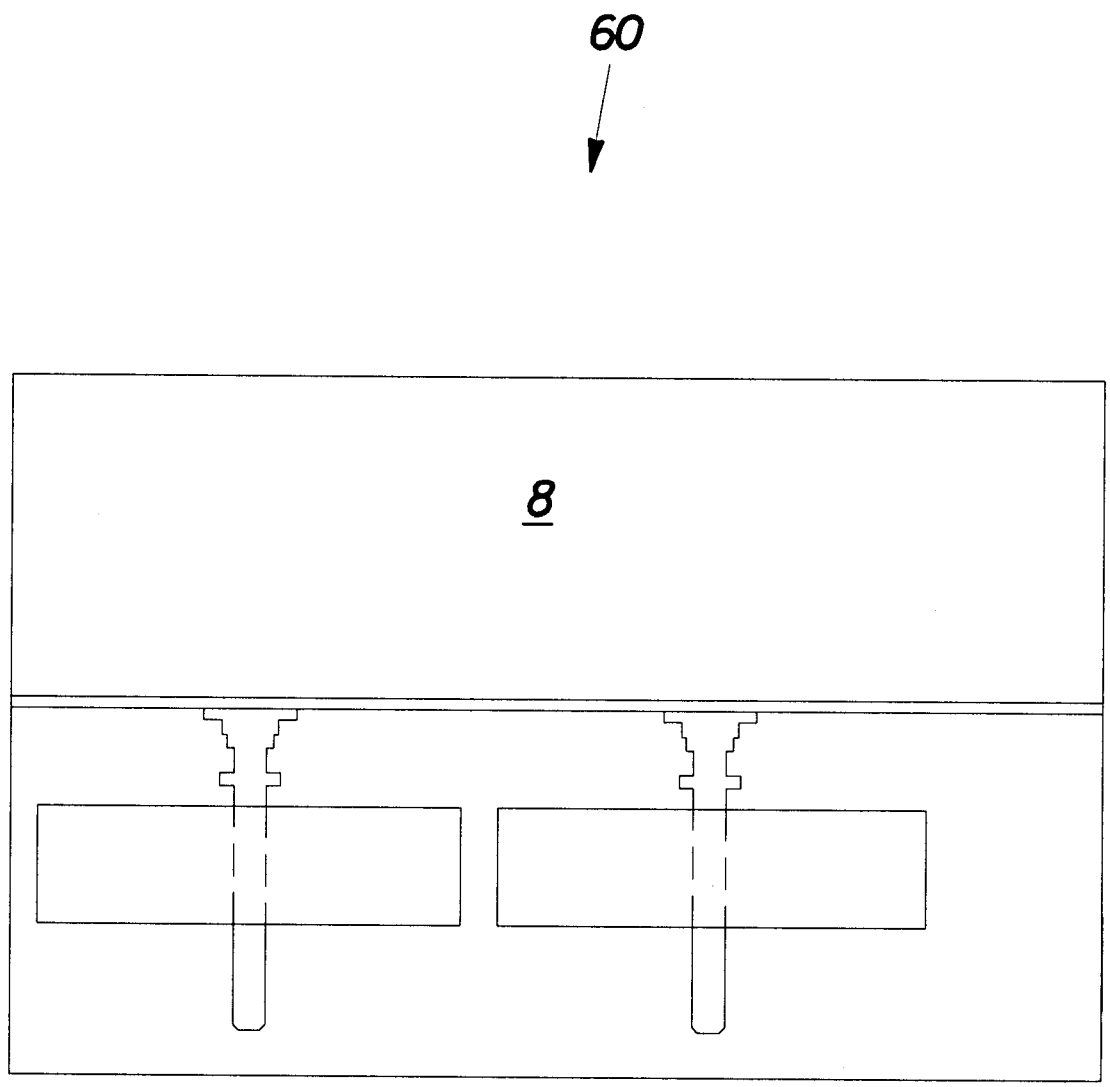
FIG. 10 is a simplified top view of the module shown in FIGS. 7–9.

As shown in FIGS. 8 and 9, electric motors, such as servo motors, dc motors, ac vector drive motors, etc., for driving the operational units may be attached to the back of the vertical plates 10 and/or 12. A "servo motor" may include a digitally controlled position servo motor and/or a digitally controlled velocity servo motor. A position servo motor is an electric motor controlled by regulating the position of an operational unit relative to a position of a reference signal and/or relative to a position of a product or a web. A velocity servo motor is an electric motor controlled by regulating the velocity of an operational unit relative to a velocity of a reference signal and/or relative to a velocity of a product or a web. FIGS. 8 and 9, for example, show motors attached to the back of the vertical plates 10 and 12. The motors may include: motors 98 and 100 for the omega rolls 68 and 70, respectively; motor 102 for the omega roll 76; motors 104, 106, and 108 for the cutting device 90; motor 110 for the omega roll 85; and motor 112 for the conveyor 94.

Figure 11:
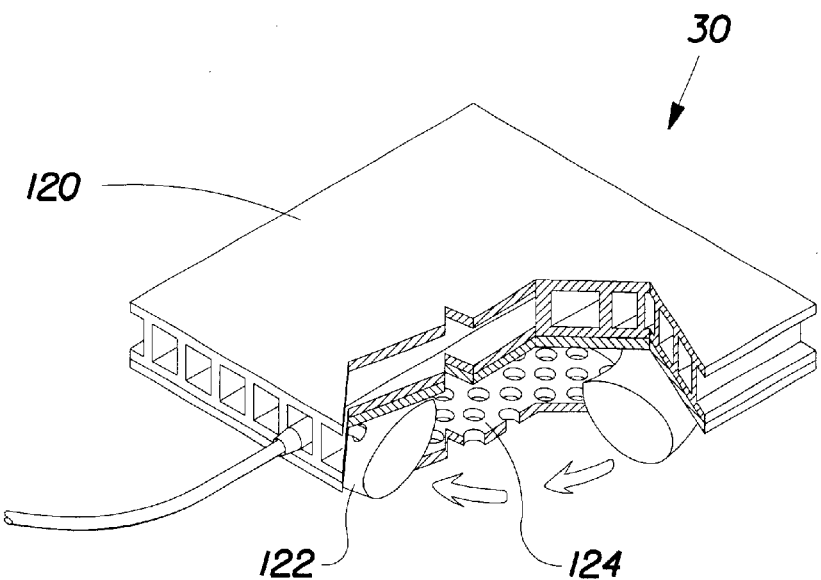
FIG. 11 is a simplified perspective view of a lifting mechanism of the present invention with a partially cut away front corner.

In a particular embodiment, a module may be moved by means of lifting mechanisms 30 inserted under the base 4 such as shown in FIGS. 1–2. The lifting mechanisms 30 may be used for smooth movements of loads over gaps in the floor surface by creating a cushion of air between the floor surface and the lifting mechanisms 30 supporting the lifted module. FIG. 11 illustrates the function of the lifting mechanism 30 supporting a load on a chamber plate 120. Compressed air or any other fluid may be pumped into a circular bag 122 that, when inflated, seals against the floor surface. (The term "air" used herein refers to any combinations of gases, including but not limited to atmospheric air.) When the air pressure in a chamber 124 exceeds the weight of the load located on the chamber plate 120, air generally slowly and evenly escapes between the circular bag 122 and the floor surface creating a cushion of air that may be, for example, about 0.003 to 0.005 inches thick. The module floats on the cushion of air and may be moved around the floor for the purpose of arranging and/or re-arranging the production line. A suitable lifting mechanism may be GAP-MASTER™ Aero-Caster manufactured by AeroGo, Inc., 1170 Andover Park West, Seattle, Wash. 98188-3909. The combined load capacity of four lifting mechanisms, for example, may be about 28,000 pounds for a 2.5 meter wide module. The ability to move the module may add flexibility to the flexible manufacturing system and allow for a change in a manufactured product in a more efficient manner. Other methods of moving modules of the present invention may include rails, fork lifts, hand trucks, wheels, cranes or any other method known in the art.

Figure 3:
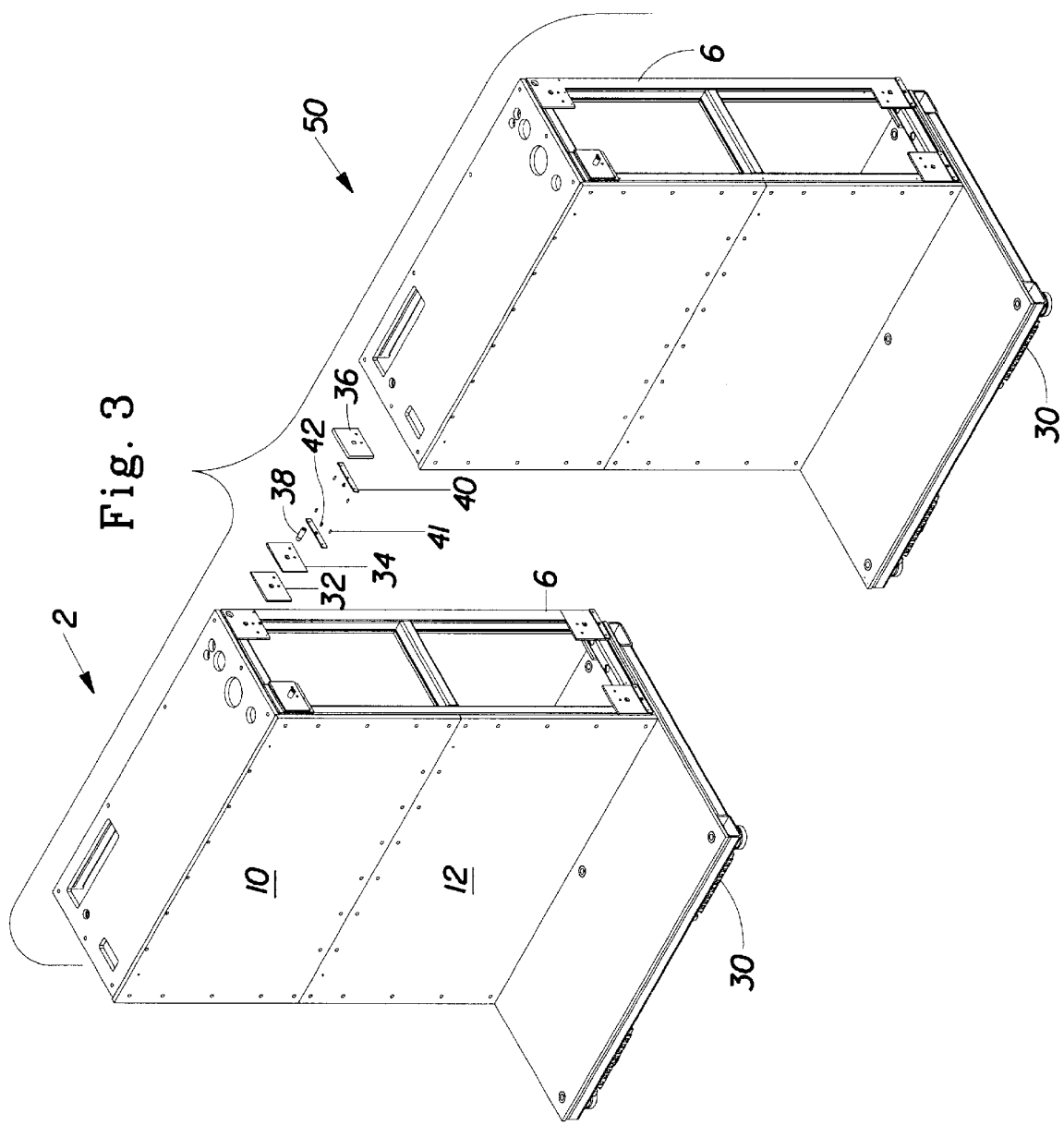
FIG. 3 is a simplified perspective view of two adjacent module frames to be attached to each other and an exploded perspective view of hardware for attaching two adjacent module frames.
Figure 4:
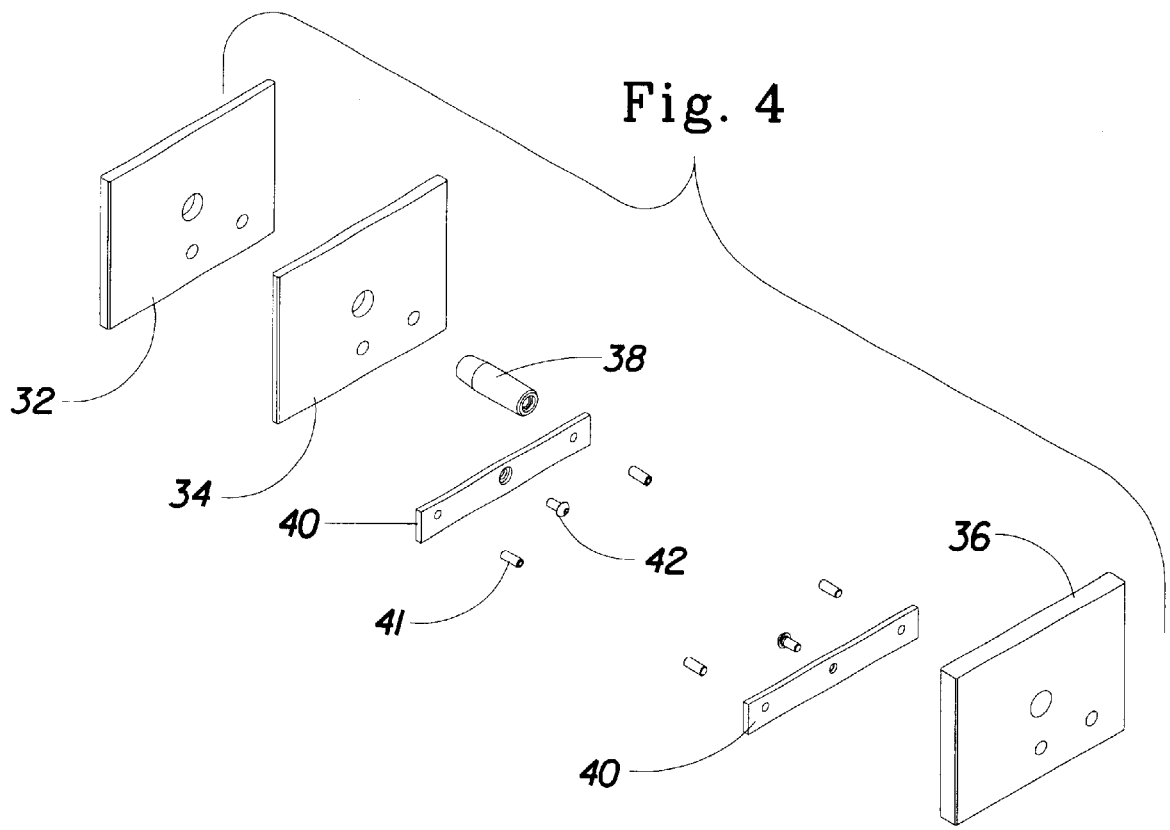
FIG. 4 is an exploded perspective view of the hardware for attaching the two adjacent module frames shown in FIG. 3.
Figure 5:
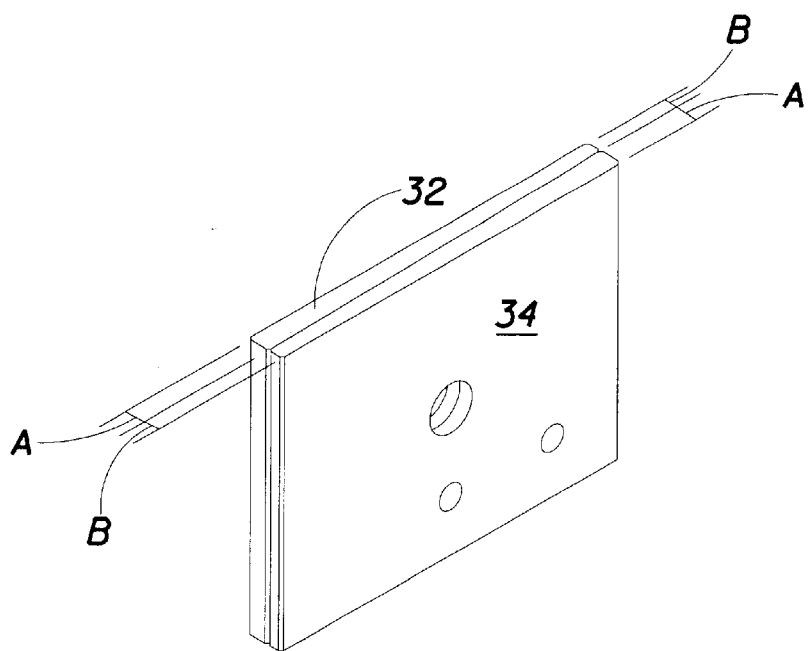
FIG. 5 is an enlarged perspective view of two paired wedges shown in FIG. 4.
Figure 6:
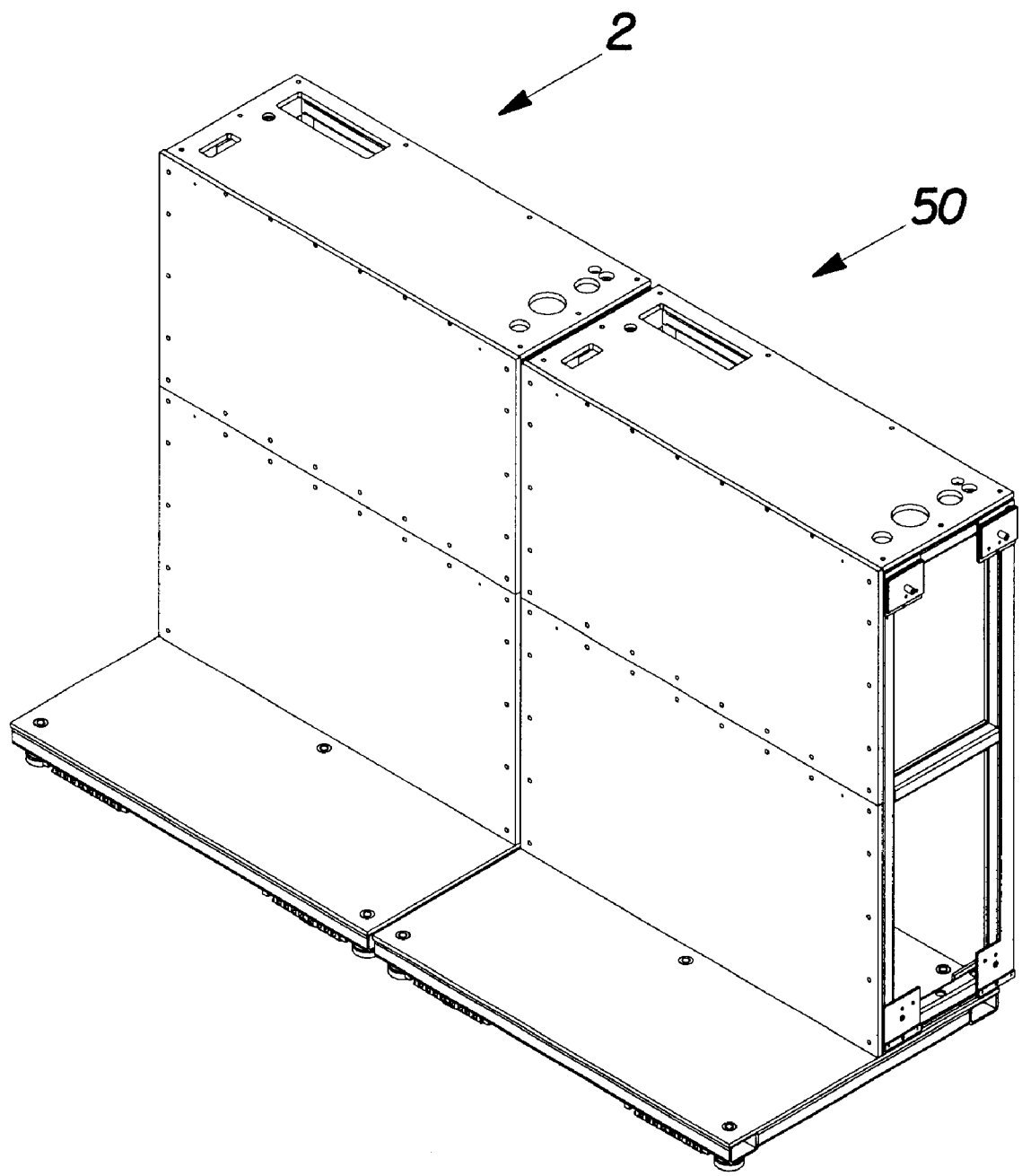
FIG. 6 is a simplified perspective view of the two adjacent module frames shown in FIG. 3 attached to each other.

After a module has been moved into a position adjacent to another module, the modules may be connected to each other at their respective side supports 6 as shown in FIGS. 3 and 6. In one particular embodiment, the side supports 6 may be substantially identical for each module. In this embodiment, the modules may be positioned with a space, such as a 20 mm space, between them in the machine direction, and a spacer 36 or a set of one or more wedges 32 and 34 may be inserted in the space created between the modules. The wedges 32 and 34, if used, may allow for easier insertion into the space between the module frames, especially, when a module frame is positioned between two other module frames. A pin 38 and two bolts may be inserted through the wedges 32 and 34 or through the spacer 36 and the corresponding side plates 28 of each of the connected module frames 2 and 50. An enlarged view of the exemplary connectors is shown in FIG. 4, and a separated view of the exemplary pair of wedges 32 and 34 is shown in FIG. 5. The bolts may be tightened with nuts to ensure a tight connection of module frames 2 and 50 as they are shown in FIG. 6. In one embodiment, one module may be joined to another module at two or more of the four corners of the side supports 6 because two or more pins may provide the alignment of the connected modules. The spacer 36 may be used on one side of the module and wedges 32 and 34 may be used on the opposite side of the module. In one embodiment, the modules may be positioned in a linear fashion along the machine direction, however, the modules may be positioned in any other arrangement. For example, modules may be arranged perpendicular to the machine direction and may assemble one or more portions of a product and feed the portion(s) of the product into the manufacturing line. The system for aligning the modules including one or more of the wedges 32 and 34, the spacer 36, the pins 38 and the bolts described above is only one embodiment. Other known means of connection and alignment may be used within the scope of the present invention.

Control System

The flexible manufacturing system of the present invention may include one or more modules and a control system that controls the operation of the one or more operational units housed in the one or more modules. An individual operational unit may include one or more motion elements, such as a motor, and/or one or more logical devices, such as a valve, solenoid, relay, gate, sprayer, nozzle, switch, light, lamp, etc. The control system may control the operation of one or more individual operational units and/or synchronize or coordinate the operation of the individual operational units to the rest of the flexible manufacturing system.

The control system may include "local control functions" and "global control functions." A "local control function" is a control function that is specific to the control within one or more modules. A local control function, for example, may include motion, drive or logic control of individual operational units within a specific group of one or more modules. "Motion control," as used in this application, refers to position control of one or more motors or profiled motion control of one or more motors such as camming or trajectory control. "Drive control" refers to continuous velocity and position control of one or more motors. "Logic control" includes using one or more logic functions to control the actuation of a logical device. A logic function may include, for example, combinational logic functions such as "if then else" functions, sequence functions, "jump to subroutine" functions, timer counter functions, etc. A local motion/drive control function, for example, may include controlling the velocity and/or position of a motor in a group of one or more modules. A local logic control function may include, for example, using logic functions to control the starting or stopping of an operational unit within a group of one or more modules, or actuating a solenoid, a reject gate or a safety disconnect switch within a group of one or more modules.

A "global control function" is a control function that pertains to synchronizing or coordinating a local control function for a particular group of one or more modules to the remainder of the flexible manufacturing system. A global control function may synchronize or coordinate a local control function to the remainder of the flexible manufacturing system, for example, by informing the local control function of an event that occurred outside of the group of one or more modules that the local control function controls, or by providing the local control function a reference signal that may be used by the local control function to synchronize or coordinate the operation of an operational unit within the group of one or more modules to the remainder of the flexible manufacturing system. A global control function may include, for example, a global motion, drive and/or logic control function that synchronizes or coordinates the operation of a local motion, drive and/or logic control function within a group of one or more modules with the operation of the rest of the flexible manufacturing system, a global start/stop logic control function that synchronizes or coordinates a local stop or start control function with the starting or stopping of the rest of the flexible manufacturing system, a global reject logic control function that synchronizes or coordinates a local reject logic control function with the rest of the flexible manufacturing system, or a global safety disconnect logic control function that synchronizes or coordinates a local safety disconnect logic control function with the rest of the flexible manufacturing system.

A global motion/drive control function that synchronizes or coordinates local motion/drive control functions is one example of a global control function. In one embodiment, for example, a global motion/drive control function may synchronize the local motion/drive control functions by providing a velocity and/or position reference signal to a local motion/drive control function that, in turn, controls a motor based upon the reference signal such as by a feedback or feed-forward control system. The reference signal may, for example, provide a velocity and/or position reference such as a digital or analog signal that ranges in amplitude, phase angle and/or frequency proportionately with the desired velocity and/or position of the overall flexible manufacturing system or of a product for synchronizing the local motion/drive functions with the overall operation of the flexible manufacturing system. This reference signal may be based upon a mechanical reference, such as a traditional master drive motor or mechanical line shaft, to which the velocity and/or position of motors within one or more groups of module(s) may be matched. Alternatively, the reference signal may be a "virtual" or electronically generated reference signal that is generated by the global motion/drive control function and provided to the local motion/drive control functions to control particular motors within the flexible manufacturing system.

A global logic control function may also coordinate the operation of local logical control functions. A global logic control function may, for example, provide start and stop signals to local logic control functions to coordinate the local logic functions to the rest of the flexible manufacturing system. A global logic control function may also provide a logic reference signal that allows the local logic controllers to control the timing of logical device operation to the rest of the flexible manufacturing line. Alternatively, a local logic control function may utilize the velocity and/or position reference signal generated by a global motion/drive control function as described above (or, a local motion/drive control function may utilize the velocity and/or position reference signal generated by a global logic control function). In one embodiment, for example, the global logic control function may provide a digital or analog signal that may range in amplitude, phase angle or frequency proportionately with the desired velocity and/or position of the flexible manufacturing system or of a product for coordinating the local logic control function with the operation of the rest of the flexible manufacturing system. As described above with respect to the global motion/drive control function, the logic reference signal may be based upon a mechanical reference or a virtual reference.

Figure 26:
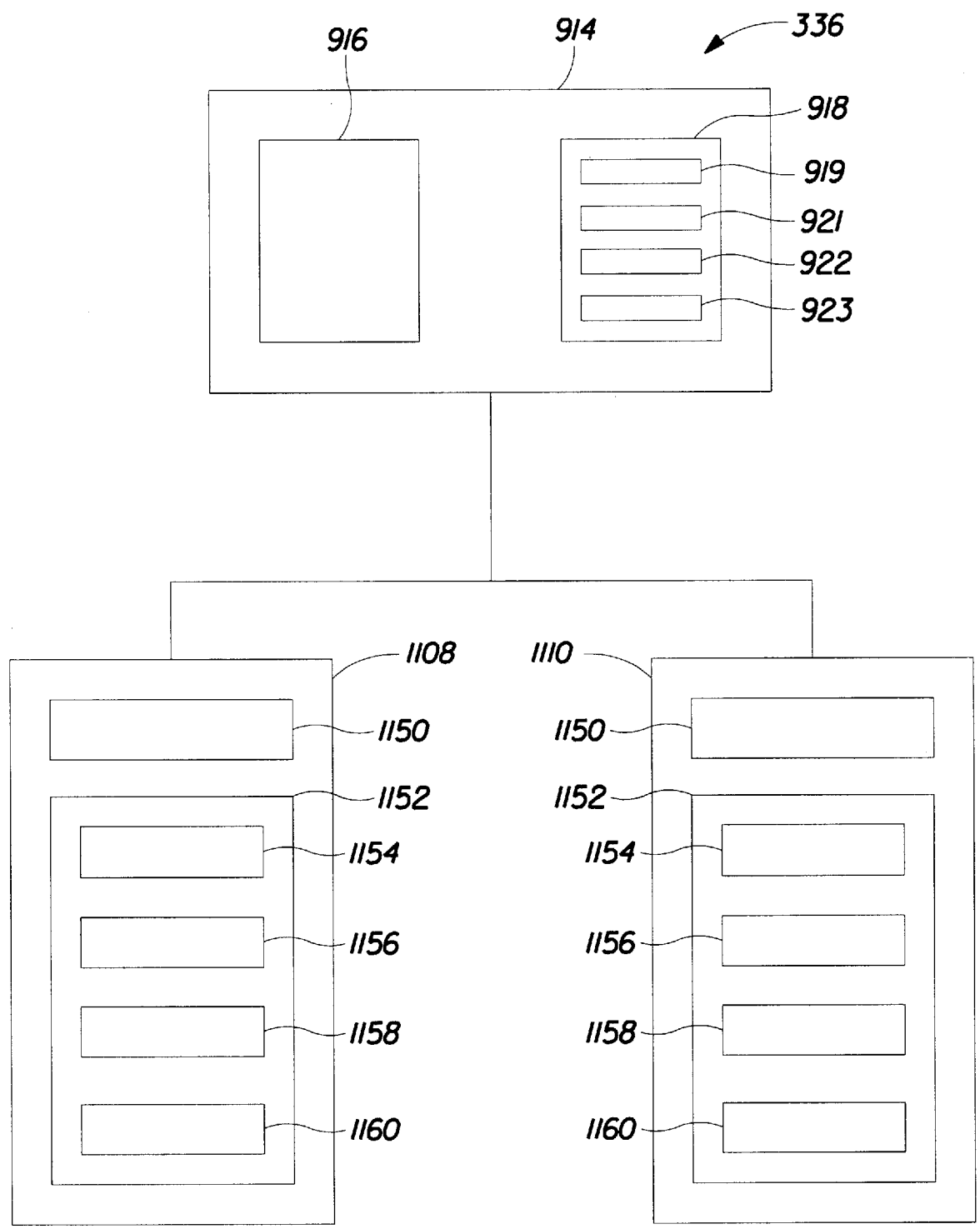
FIG. 26 is an example of one embodiment of a standard central computer panel.

The global control functions and local control functions may be performed by or reside in a central computer, a local controller or a combination of a central computer and one or more local controllers. In one embodiment, the control system may include a central computer that performs global control functions and one or more local controllers that each perform local control functions for a particular group of one or more modules. In FIG. 26, for example, exemplary global control functions and local control functions are depicted in the form of a block diagram. In this embodiment, the global control functions reside in the central computer 336, which may comprise software and/or hardware to perform global control functions such as a global motion/drive control function 916 and/or a global logic control function 918. Examples of a global logic control function include a global operator interface control function 920, a global start/stop control function 921, a global reject control function 922, and a global safety disconnect function 923. The local control functions may reside in local controllers, such as 1108 and 1110, which may comprise software and/or hardware to perform local control functions such as a local motion/drive control function 1150 and/or a local logic control function 1152. Examples of a local logic control function include a local operator interface control function 1154, a local stop/start control function 1156, a local reject control function 1158 and a local safety disconnect control function 1160. In another embodiment, the central computer may perform both the global control functions and the local control functions for controlling the operation of one or more groups of module(s). In this embodiment, the central computer may comprise an integrated platform with local control software distributed on a per module or per group of modules basis, i.e., the software performing the local control function for one module or one group of modules may comprise a separate control routine or data block. Although the separate control routine or data block may include calls to shared subroutines or may include shared data, the separate control routine or data block preferably includes at least one portion that is distinct to a particular module or group of modules so that the control routine or data block for that module or group of modules may be easily located in the event that the module or group of modules is modified, moved within, added to or removed from the flexible manufacturing system. In yet another embodiment, the control system may include two or more local controllers without a central computer. In this embodiment, the local controllers each perform the local control function for a particular module or group of modules. In addition, one or more of the local controllers perform the global control functions for the overall flexible manufacturing system as well as the local control functions for a module or group of modules.

Figure 25:
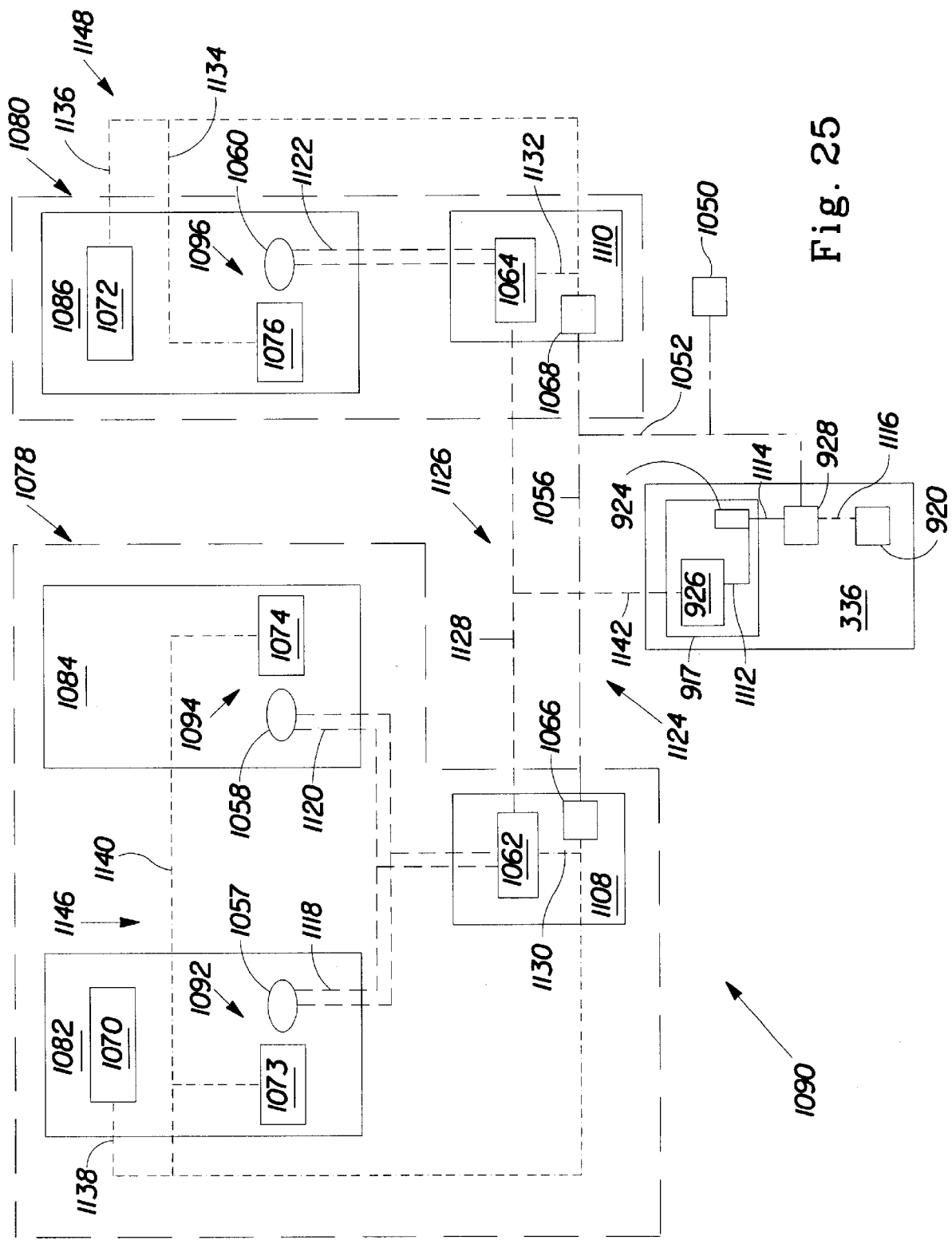
FIG. 25 is a block diagram of a communication network showing a central computer that may be used to synchronize two groups of module(s).

In the embodiment shown in FIGS. 25 and 26, for example, the central computer 336 may perform the global motion/drive control function 916 that synchronizes the operation of local motion/drive control functions 1152. In this embodiment, the central computer 336 may provide a reference signal that a local motion/drive controller may use to synchronize one or more motors that the local motion/drive controller is controlling. A "motion/drive controller" refers to a microprocessor-based system that controls the current, velocity and/or position of one or more motors. A motion/drive controller may also synchronize the operation of one or more motors such as by utilizing a reference signal provided by a global motion/drive control function. The motion/drive controller may, for example, control the velocity and/or position of a servo motor, a dc motor, an ac vector drive motor, etc. A motion/drive controller may also be capable of being integrated into a network of motion/drive controllers that synchronize one or more motors to a master machine velocity and position. The central motion/drive controller 917 may directly control individual motors in a flexible manufacturing system or may provide a velocity and/or position reference signal over a network to one or more local motion/drive controllers. Each local motion/drive controller, such as local motion/drive controllers 1062 and 1064, may utilize the reference signal to synchronize the motor(s) that it directly controls to the rest of the flexible manufacturing system. The central motion/drive controller 917 may, for example, include a master motion/drive reference 924 and a motion/drive control signal converter transmitter 926. The master motion/drive reference 924 may provide a reference signal that may be used to synchronize the operation of a module or a group of modules to the rest of the flexible manufacturing system. The master motion/drive reference 924 may be connected to a central motion/drive control signal converter transmitter 926 by a motion/drive reference link 1112 and to a central logic controller 928 by a motion/drive reference link 1114. The motion/drive reference links 1112 and 1114 may, for example, be variable frequency, phase angle and/or amplitude links. The central logic controller 928 may be connected to a central operator interface 920 by a network link 1116.

The global motion/drive control function may generate a virtual reference signal via solid state electronic hardware and/or software, which may be immune from mechanical disturbances such as backlash and/or friction. In one embodiment, the master motion/drive reference 924 may provide a virtual reference velocity and/or position signal for synchronizing the operation of a group of one or more modules to the rest of the flexible manufacturing system. The master motion/drive reference 924 may, for example, serve as an electronic encoder or resolver simulator and produce a signal comprising a series of pulses having a frequency that is relative to the desired velocity and/or position of the production line. The pulses may be configured in quadrature such that the master motion/drive reference signal is multiplied by four to obtain a higher resolution and accuracy. The pulses may also be converted into a serial format and transmitted over a network via a serial link to multiple local motion/drive controllers.

In one embodiment, the central computer 336 may include a velocity input pre-programmed into the central computer 336 or may accept a velocity reference input from the central operator interface 920 via the central logic controller 928 or from one or more of the local operator interfaces such as 1070 and 1072. In this embodiment, the central computer 336 may convert the velocity reference input into an input signal to the master motion/drive reference 924 using an algorithm in the central logic controller 928. Further, the central computer 336 may vary the input signal provided to the master motion/drive reference 924 or other master machine reference hardware. The algorithm, for example, may vary the input signal provided to the master motion/drive reference 924 while the machine is moving so that the line can ramp up and down to predefined set points pre-programmed in the central computer or entered by the operator on an operator interface 920.

In an alternative embodiment, the master motion/drive reference signal may originate from a master drive motor or from a mechanical line shaft. In one embodiment, the master motion/drive reference signal may be proportional to the velocity and/or position of a master drive motor or a mechanical line shaft in the flexible manufacturing system. The central computer 336 may, for example, receive a motor reference signal such as from an encoder or a resolver mounted on the master drive motor or the mechanical line shaft. The motor reference signal may then be converted to or used as a master motion/drive reference signal and distributed via a network such as the motion/drive control sub-network 1126. A local motion/drive controller, such as the first local controller 1062, may use this master motion/ drive reference signal to control the velocity of drive motors in that module or group of modules. An exemplary control signal that may be generated as the master motion/drive reference signal is described in U.S. Pat. No. 5,383,988 entitled "Modular Apparatus for Fabricating an Absorbent Article," issued to Thomas R. Herrmann et al. on Jan. 24, 1995, which is incorporated by reference.

A "logic controller" refers to a microprocessor-based system that uses logic functions to control the actuation of and/or synchronization of logical devices such as solenoids, relays, valves, gates, sprayers, nozzles, switches, lights, lamps, etc. In one embodiment, a logic controller may be capable of being integrated into a network of logic controllers to pass information for the purpose of integrated logic control. The central logic controller 928 may directly control individual logical devices in a flexible manufacturing system and/or may provide a reference signal to a network of local logic controllers, such as local logic controllers 1108 and 1110, that directly control the logical devices of the operational units within groups of one or more modules of the flexible manufacturing system. The global logic function 918 may be performed by a central logic controller 928. The central logic controller 928 may generate a velocity and/or position reference from pre-defined set points programmed into the central logic controller or from an operator interface, such as the central operator interface 920, and control the reference via software in the central logic controller 928. The central logic controller 928 may be integrated into a logic control network 1124 with the first and second local logic controllers 1066 and 1068, respectively, by logic control network links 1052 and 1056. A standard series of software steps that performs functions such as logic control and information processing may be integrated in the logic controllers. In one embodiment, for example, the central and/or local logic controllers may include a programmable logic controller ("PLC") in which a standard series of software steps that perform control functions and information processing are integrated into the PLC. In another embodiment, however, the central and/or local logic controllers may include a personal computer ("PC"), a mainframe, a micro computer or a mini computer in which flowchart programming techniques may be utilized to perform control functions and information processing.

The central logic controller 928 may function as a network system integrator. Information generated in one or more of the local controllers 1108 and/or 1110 may be passed to the central computer 336 via a digital or analog network. The central logic controller 928 may integrate the starting and stopping of one or more groups of module(s) by transmitting signals to and from the one or more local controllers over the network. In addition, the central logic controller 928 may also control a power distribution system and/or integrated safety systems via the network. Further, the central logic controller 928 may monitor and control utilities for supporting operational units, such as adhesive tanks, vacuum systems, compressed air, glycol, etc. The central logic controller 928 may also accumulate production data information, such as a number of products made, a mean time between failure, a line efficiency, etc., and display the information on the main operator interface or transmit the information to the individual local controllers.

The central computer 336 may include multiple hardware components that perform distinct control functions, or may comprise a single multi-function computer to perform some or all of the various control functions. The central computer may, for example, include a combination of a an Encoder Signal Reference Simulator (ESRS) manufactured by Rockwell International and a programmable logic controller such as a 1785-L40C PLC5 manufactured by Rockwell to perform the global motion/drive control function 916 and the global logic control function 918. Alternatively, the central computer may include a programmable logic controller ("PLC") to perform the global logic control function 918, and a personal computer ("PC") to perform the global motion/drive control function 916. In this embodiment, for example, either the PLC or the PC may perform the global operator interface function 921. Alternatively, the central computer 336 may include a single multi-function computer system such as a personal computer, mainframe, microcomputer, mini-computer, etc. that performs each of the global motion, drive and logic control functions, and the global data collection and reporting function.

Figure 13:
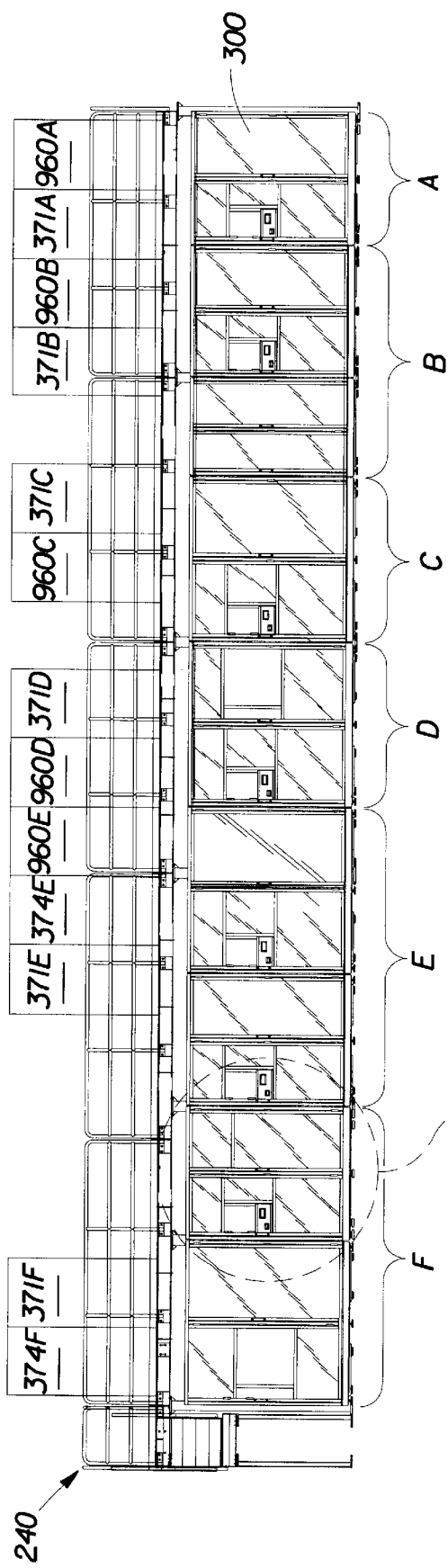
FIG. 13 is a simplified view front from the operator side of a modular converting line of a flexible manufacturing system of the present invention including a panel support structure.

In addition, the various pieces of hardware that may comprise the central computer 336, may be housed in a single panel or may include multiple components in different panels that are located adjacent to each other or distributed throughout the manufacturing system. In one embodiment, for example, the panel that houses a central motion/drive controller may be located close to a master drive motor or a mechanical line shaft if one of these methods of creating a master motion/drive reference signal is used, while the panel that houses the central logic controller may be located in another panel somewhere else along the flexible manufacturing system. The central computer 336 may be housed in one or more control panels such as the central computer control panel 914 shown in FIG. 26. The central computer control panel 914 that houses the central computer 336 may be located on the panel support structure 240 such as shown in FIG. 13 or in another area of the flexible manufacturing system.

A local controller may control the operation of one or more operational units housed in a module or a group of modules. A local controller may include a local motion/drive controller and/or a local logic controller. FIG. 25, for example, shows a simplified view of one embodiment of a flexible manufacturing system of the present invention including a control system 1090 for two groups of one or more modules 1078 and 1080. For ease of illustration, FIG. 25 depicts only a central computer 336 and two groups of one or more modules 1078 and 1080. A flexible manufacturing system of the present invention, however, may include one, two, three or more groups of one or more modules. In the flexible manufacturing system shown in FIG. 25, the first group of modules 1078 includes a first and a second module 1082 and 1084, respectively, and the second group 1080 includes a third module 1086. In this embodiment, the control system 1090 preferably includes a central computer 336, and first and second local controllers 1108 and 1110 for controlling the operational units of the first and second groups of module(s) 1078 and 1080, respectively. The first local controller 1108 may include a first local motion/drive controller 1062 and/or a first local logic controller 1066. The second local controller 1110 may include a second local motion/drive controller 1064 and/or a second local logic controller 1068. The first local controller 1108 and/or the second local controller 1110 may also include a local operator interface such as 1070 and 1072.

Each module may include one or more operational unit(s): the first and second modules 1082 and 1084 of the first group 1078 may comprise a first operational unit 1092 and a second operational unit 1094, and the module 1086 of the second group 1080 may comprise a third operational unit 1096. Each operational unit may comprise one or more motor(s) and/or one or more control device(s). (The term "control device" as used in this application refers to devices such as a solenoid, a photo eye, a proximity switch, a temperature sensor, a relay, a small AC motor for driving a web tracking mechanism, or any other control device known in the art.) The first and second operational units 1092 and 1094 may comprise first and second motors 1057 and 1058, and first and second control devices 1073 and 1074. Similarly, the third operational unit 1096 may comprise a third motor 1060 and a third control device 1076.

The first and second local controllers 1108 and 1110 may be integrated into a network with the central computer 336. The network may include, for example, two sub-networks: a motion/drive control sub-network 1126 by which the central motion/drive controller 916 is connected via links 1128 and 1142 to the first and second local motion/drive controllers 1062 and 1064, respectively, and a logic control sub-network 1124 by which the central logic controller 928 is connected via links 1052 and 1056 to the first and second local logic controllers 1066 and 1068, respectively. The information transmitted over the motion/drive control sub-network 1126 may, for example, represent the distances that the master drive encoder or a virtual master drive encoder has moved. Information transmitted over the logic control sub-network 1124 may, for example, include machine set points, product quality information, machine status and run condition, etc.

As described above, a group of one or more modules may include one or more operational units. Each operational unit may include at least one motor and/or at least one logical device. In one embodiment of the present invention, the motor may be an independently-driven servo motor. In this embodiment, the velocity and position of operational units need not be phased by a common mechanical line shaft. There may be no mechanical coupling between the operational units, and the velocity and position of the operational units may be synchronized by the local controller with respect to a common positional and/or velocity reference. The source of the common reference may be any of the master motion/drive references described above.

The motion/drive controllers may be connected to one or more servo motor(s). In the embodiment shown in FIG. 25, for example, the first local motion/drive controller 1062 may be connected with the servo motors 1057 and 1058 of the first and second modules 1082 and 1084 of the first group 1078 by power and feedback cables 1118 and 1120, and, similarly, the second local motion/drive controller 1064 may be connected with the servo motor 1060 located in the third module 1086 of the second group 1080 by power and feedback cables 1122.

A motor motion/drive control system may include, for example, one or more of the following component(s): a local motion/drive controller; an electric motor such as a servo motor, a dc motor an ac vector drive motor, etc.; and/or an electric motor position feedback sensor such as an encoder or a resolver. The local motion/drive controllers 1062 and 1064 may include one or more programmable motion/drive controllers and one or more power converter/amplifier. A programmable motion/drive controller may control a motor using a specific control routine or configuration that includes a set of pre-programmed or operator defined control steps or set points. The control steps or configuration may, for example, include instructions on the relative velocity and/or position of one or more motors to a master reference signal. A position feedback sensor for the motor shaft may also be connected to the programmable motion/drive controller. The programmable motion/drive controller may calculate the position of the servo motor shaft relative to a master reference signal using the feedback sensor, and follow pre-programmed instructions to adjust the velocity and/or position of the motor to match the relative velocity and position of the master reference signal. In one embodiment, for example, the master reference signal may include a frequency, amplitude and/or an angle to represent the reference velocity and position for the flexible manufacturing system. A motor power converter/amplifier may control the amount of electrical current applied to the motor to maintain its relative position to the master reference signal. The amount of electrical current required may be determined by the motion/drive controller and may be based on the amount of error calculated between the motor's shaft and the relative velocity and/or position of the master reference. The motion/drive controller may also transmit, via an analog or digital network, to the logic controller information such as status codes, error codes, velocity and position.

In order to assist in line changeovers, product size variations, etc., the programmable motion/drive controller may have several alternative routines from which a line operator may choose to configure the line to assemble a particular product. Alternatively, the control routines may use operator-defined set points to control the operation of various motors in a group of one or more module(s). In a further embodiment, if the programmable motion/drive controller may be connected to a network as shown in FIG. 25, and the control routines may be replaced, deleted or modified over the network. The network, in one embodiment, may be an ethernet, a Control Net™ (a product of Rockwell International), a combination of the two, or any other type of network known in the art.

The motor may be mechanically connected to one or more operational unit(s) and electrically connected to the motor power converter/amplifier. The mechanical interface between the motor and the operational unit may be a gear or a pulley set and/or a combination, or it may be a direct link. Operational units that are required to be pitched to a product, i.e., phased once, twice, etc. per product, on the production line may have motors that are configured as "pitched" motor systems to rotate at a velocity that is synchronized with the product pitch. In one embodiment, an operator may synchronize the velocity of the motor with the product pitch by selecting the number of encoder pulses of a line shaft or a master drive motor on the converting line or the number of virtual encoder pulses transmitted over the motion/drive control network that represent a single product pitch at the operator interface. The local motion/drive control function may synchronize the operation of a pitched operational unit to a single product length. For example, a single revolution or linear movement of the pitched operational unit may correspond to an integer number of product lengths, or an integer number of revolutions or linear movements of the pitched operational unit may correspond to a single product length. In one embodiment, a local controller may synchronize the rotation or linear movement of the pitched operational unit to a single product length by multiplying the set number of encoder or virtual encoder pulses by the gear ratio for the particular motor that drives that operational unit. The gear ratio is dependent upon the mechanical connection between the motor and the operational unit, and the number of products that may be produced by one rotation or linear movement of the operational unit. The gear ratio may be pre-programmed or set by an operator for a particular motor. In an alternative embodiment, the rotational or linear velocity of the operational unit may be synchronized with the product pitch by preprogramming, or by the operator selecting at the operator interface, the number of products that will be produced in a given time frame, e.g., 100 diapers per minute. Operational units that are not required to be pitched to the product may have motors that are mechanically coupled to the non-pitched operational units and may be configured as non-pitched motor systems. The non-pitched operational unit may follow the relative velocity of the master reference. The operator may have the ability to change or adjust the motor velocity of the non-pitched operational unit to compensate for various changes in raw materials and/or a product size, or this may be done through programming.

An independently-driven servo motor allows for more rapid changes in motor velocity and position versus the remainder of the line because software control of the servo motor may be more rapidly changed out than traditional mechanical linkages, gears, belt drives, etc. Using digitally controlled servo motors may also allow for more accuracy in product making because they may provide a higher degree of synchronization and position control over traditional line shaft and/or belt drives, especially in a long drive train. Furthermore, digitally controlled servo motors may also allow for "push button" changeovers that allow an operator to select a product from pre-configured program set points for one or more of the logic and motion/drive control systems to direct the motion/drive of one or more of the servo motors to automatically make the desired product.

As described above, an operational unit may include one or more logical devices. In one embodiment, the local logic control functions may be housed in a local logic controller that directly controls the operation of the logical devices for a particular group of one or more modules and synchronizes or coordinates the operation of those logical devices with the rest of the flexible manufacturing system. The local logic controller may synchronize or coordinate the operation of the local logical devices by using a master logic reference signal that is generated by the central logic controller and transmitted over a network, such as the logic control sub-network 1124, to the local logic controller.

The local logic controllers may be connected with one or more control devices and/or one or more operator interfaces in a remote local network. The first local logic controller 1066 may, for example, be connected with the first and second control devices 1073 and 1074 located in the first and second modules 1082 and 1084 of the first group of modules 1078 and with a first operator interface 1070 by the remote local network links 1138 and 1140. Similarly, the second local logic controller 1068 may, for example, be connected with the third control device 1076 located in module 1086 of the second group 1080 and with a second operator interface 1072 by the remote local network links 1134 and 1136. The remote local networks may be a digital internal control network for a group of one or more modules. This remote local network may originate at a local logic controller and connect the operational unit control devices with the logic controller via remote input and output electronic modules. The first local logic controller 1066, for example, may be connected to the first and second operational unit control devices 1073 and 1074 via the remote local network 1146. The second local logic controller 1068, for example, may be connected to the third operational unit control device 1076 via the remote local network 1148. The internal network may also connect the local logic controller with its corresponding operator interface such as the first and second local logic controllers 1066 and 1068 with the first and second operator interfaces 1070 and 1072, respectively. Signals transmitted over a remote local network may include, for example, status from control devices located in one or more of the modules included in a group of module(s).

Figure 30:
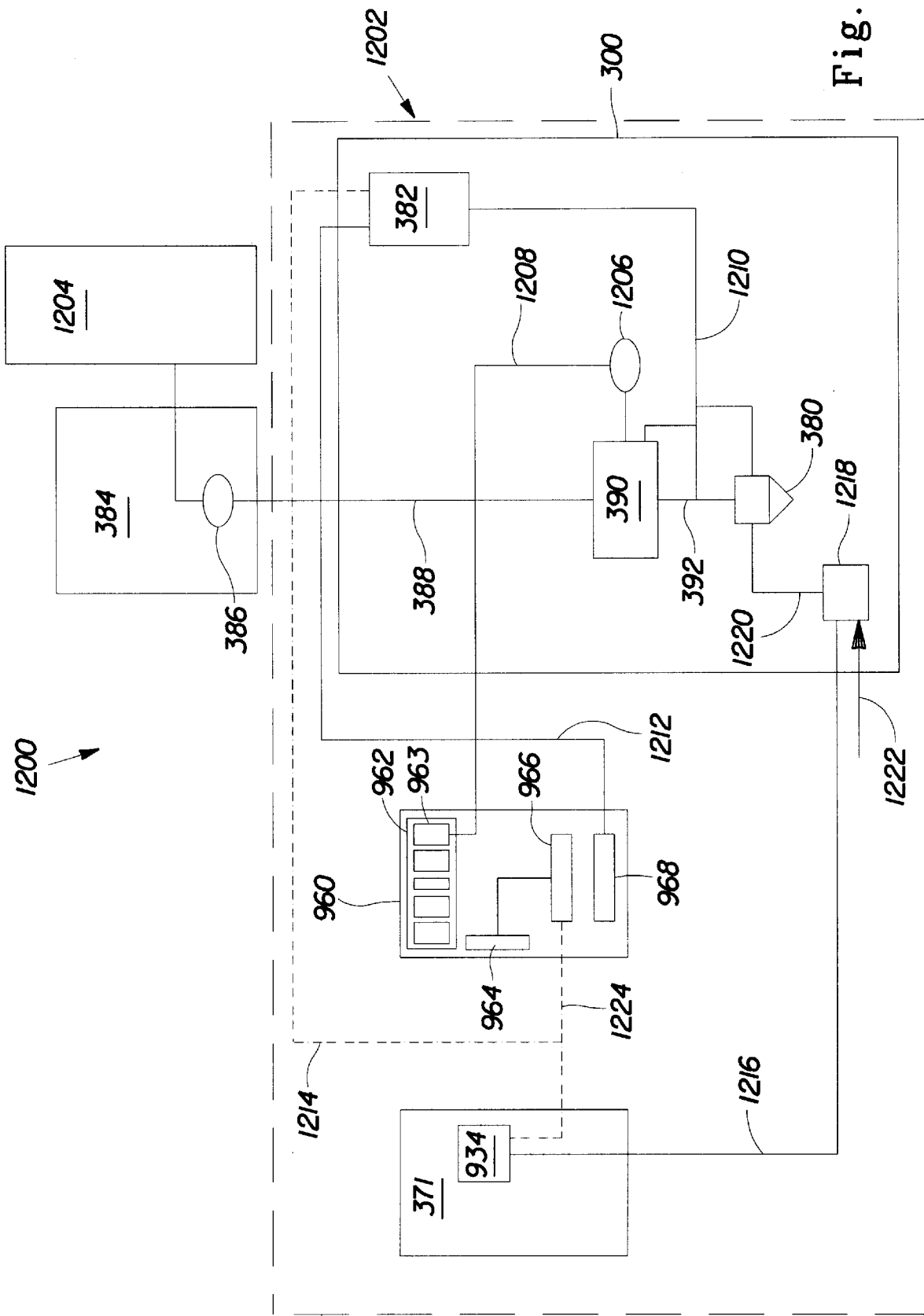
FIG. 30 is a block diagram of an adhesive control system.

An example of a local control system including both a local motion/drive control function and a local logic control function is the adhesive control system shown in FIG. 30. A group of one or more modules 1202 of the present invention may include one or more adhesive applicators 380 housed in a module 300. The adhesive applicator 380 may be of any type used in the art and may receive adhesive from an adhesive tank 384 via a pump 386, a supply hose 388, a remote meter 390, and an adhesive supply hose 392. The remote meter 390 may be driven by a servo motor 1206, which may be controlled by the local motion/drive controller 962. The local motion/drive controller 962 may include multiple, independent single axis programmable motion/drive controllers 963 such as 1398-DDM-009 controllers manufactured by Rockwell International for each motor that is to be controlled, or one or more multiple axis programmable motion/drive controllers such as a 1394-SJT10-T-RL controller manufactured by Rockwell International that may control multiple motors. The local motion/drive controller 962 may control the servo motor 1206 via a drive and feedback control cable 1208. An adhesive supply hose 392 may supply the adhesive from the remote meter 390 to the adhesive applicator 380. The temperature of the adhesive in the remote meter 390, the adhesive supply hose 392 and the adhesive applicator 380 may be controlled by the local logic controller 934 via a power and feedback cable 1210, which may be connected to the local logic controller 934 through an adhesive junction box 382 and remote local network link 1214. The adhesive junction box 382 may have terminal connectors for an electrical power supply and input/output devices for temperature control/feedback signals from the remote meter 390, the adhesive supply hose 392 and the adhesive applicator 380. The adhesive junction box 382 may be connected to interface connectors 968 via a power supply cable 1212, and to the local logic controller 934 via a remote local network link 1214 to provide a temperature feedback signal to the local logic controller 934. The local logic controller 934 may be connected, such as by an adhesive stitching control cable 1216, to an electrical-to-pneumatic converter 1218 located in the module 300. The converter 1218 may be connected to the adhesive applicator 380 via compressed air tubing 1220. The converter 1218 may receive compressed air 1222 and provide on/off supply of compressed air to the adhesive applicator 380 for starting and stopping the adhesive flow through the adhesive applicator 380.

In one particular embodiment of the present invention, a standard adhesive control panel 960 may be configured containing standard hardware and/or software for controlling the operation of adhesive applicators throughout the flexible manufacturing system. A standard adhesive control panel 960, for example, may be used for each group of one or more modules of the flexible manufacturing system of the present invention that includes an adhesive applicator. The specific hardware and/or software required for controlling a particular adhesive applicator such as adhesive applicator 380 may be included with the local logic controller 934, and/or may be added to the standard adhesive control panel 960. Utilizing standard adhesive panels may allow adhesive operational units to be added or removed from a group of one or more modules without reconfiguring the local controller. In this embodiment, for example, the local logic controller 934 may be connected to a logic control panel input and output section 966 located in the adhesive control panel 960 via a remote local network link 1224. A standard adhesive control panel 960 is shown schematically in FIG. 29. The adhesive control panel 960 may have a standard design for controlling multiple remote meters by including multiple programmable motion/drive controller and motor power converter/amplifier pairs 962.

The tank control function may be performed by a separate local controller dedicated to controlling one or more adhesive tanks, one or more of the local controllers or by the central computer. The tank control function may control the temperature of the adhesive in the tank 384 and in the supply hose 388 in addition to the rate of the adhesive supplied to the remote meter 390 located in the module 300 of the group of one or more modules 1202. The adhesive tank 384 may include multiple adhesive chambers that each include at least one pump and may contain different types of adhesives.

A local controller may include at least a logic controller and/or a motion/drive controller and/or other elements such as one or more safety circuits and/or one or more power distribution systems. As shown in FIG. 27, for example, a control panel 370 may include a motion/drive controller 932; a logic controller 934; control relays 936; safety relay 938; a programmable cam switch 940, dedicated wire termination points 942; interface connectors 944; a logic interface panel 946; power distribution circuit breakers 948; motion/drive controller contactors 950; AC motor contactors 952; and 25VDC power supplies 954. A local controller may be housed by one or more control panels or by one or more of the modules of a group of module(s).

In one embodiment of the present invention, a local controller may be housed in one or more standard control panels such as described above with respect to the central computer 336. A standard control panel that houses a local controller may be located nearby or adjacent to the module (s) that the local controller controls. As shown in FIG. 15, for example, a standard control panel 370 may be located on the panel support structure 240 adjacent to the module 300 that it controls. In the event that the module(s) are replaced by another group of one or more modules, the standard control panel 370 may be reconfigured to operate as the local controller for the new group of module(s) and to control the new module(s).

In one embodiment, the flexible manufacturing system of the present invention may include standard main control panels 371 as shown in FIGS. 13 and 27 and standard auxiliary control panels 374 (standard auxiliary control panels 374E and 374F are shown in FIG. 13). Each of the standard control panels may be limited in space so that it may only house control hardware for a fixed number of electric motors, logical devices, etc. In this embodiment, when a group of module(s) includes more than the fixed number of electric motors, logical devices, etc. than a standard main control panel 371 may house, one or more standard auxiliary control panels 374 may also be used. In addition, a standard adhesive control panel 960, such as shown in FIGS. 13 and 27, and described above, may be used to house the hardware for a particular local controller that controls an adhesive system in the group of one or more modules. Alternatively, additional standard control panels may be configured to contain the hardware that controls other subsystems of a group of one or more modules such as motion/drive or logic control aspects of the local controllers.

Figure 14:
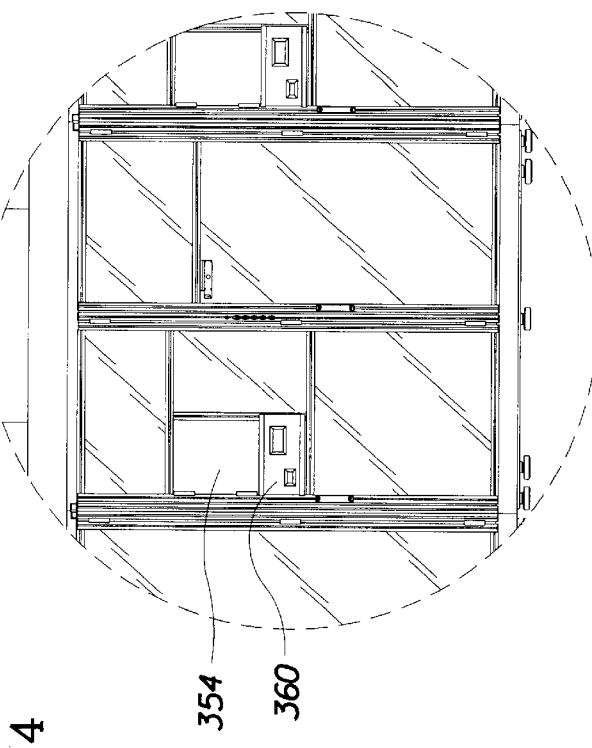
FIG. 14 is an enlarged front view of a module shown in FIG. 13.
Figure 17:
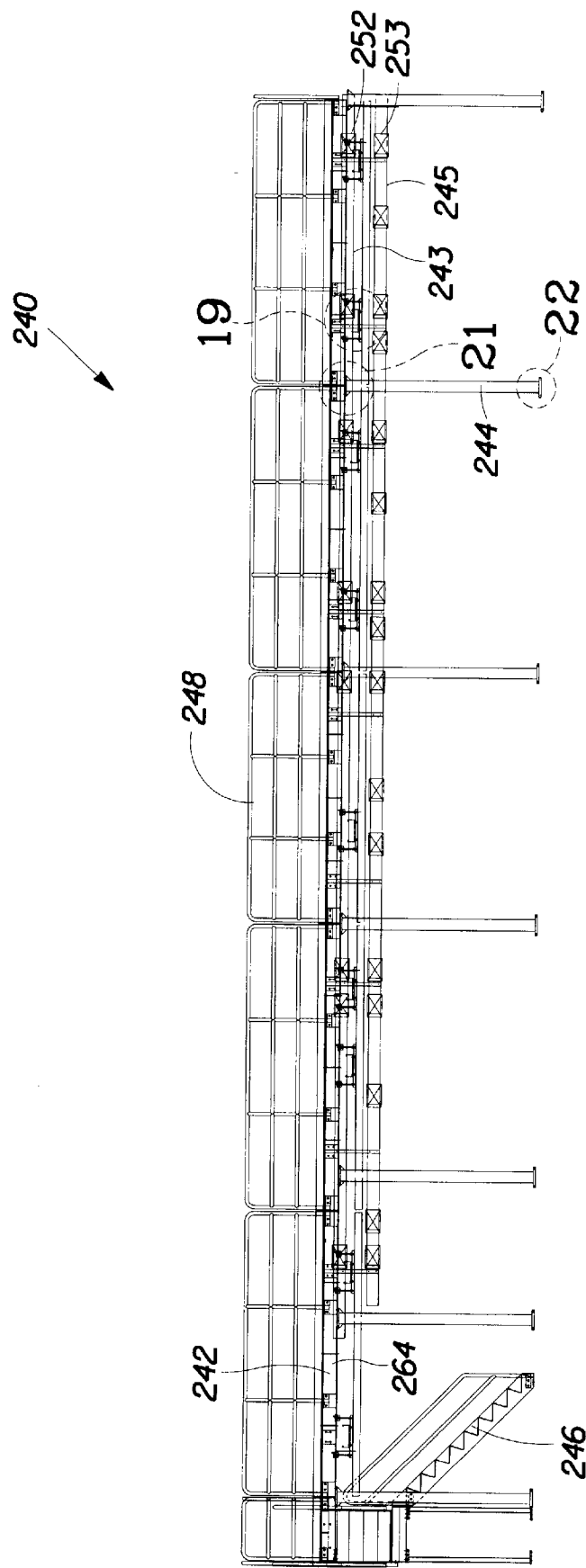
FIG. 17 is a simplified front view of the panel support structure shown in FIGS. 13 and 15.

FIGS. 13 and 14 show, for example, a portion of an exemplary flexible manufacturing system of the present invention in which the local controllers are housed in standard control panels on a panel support structure 240 adjacent to the modules that the local controllers control. The module A is shown adjacent to a standard main control panel 371A and a standard adhesive control panel 960A that together comprise the local controller for the module A. The group of modules B is shown adjacent to a standard main control panel 371B and a standard adhesive control panel 960B that together comprise the local controller for the group of modules B. The module C is shown adjacent to a standard main control panel 371C and a standard adhesive control panel 960C that together comprise the local controller for the module C. Next, the module D is shown adjacent to a standard main control panel 371D and a standard adhesive control panel 960D that together comprise the local controller for the module D. The group of modules E is shown adjacent to a standard main control panel 371E, a standard auxiliary control panel 374E and a standard adhesive control panel 960E that together comprise the local controller for the group of modules E. Finally, the group of modules F is shown adjacent to a standard main control panel 371F and a standard auxiliary control panel 374F that together comprise the local controller for the group of modules F.

The term "operator interface" as used in this application refers to a microprocessor-based system that may allow an operator to input data and receive data from a central computer or from a local controller. A flexible manufacturing system of the present invention may include a central operator interface that may be connected to the central computer and one or more local operator interfaces that may be connected to one or more local controllers. The central operator interface may obtain information from the central logic controller in the central computer and may integrate the line data from one or more local controllers and display the data for the operator. The central operator interface may also distribute the data input from the operator to one or more local controllers. An operator interface may also be the origin of one or more machine set points such as motor parameter set points, glue temperatures, and programmable cam limits. The operator interface may also hold a database for other displays on the line, such as electronic annunciation systems.

Figure 23:
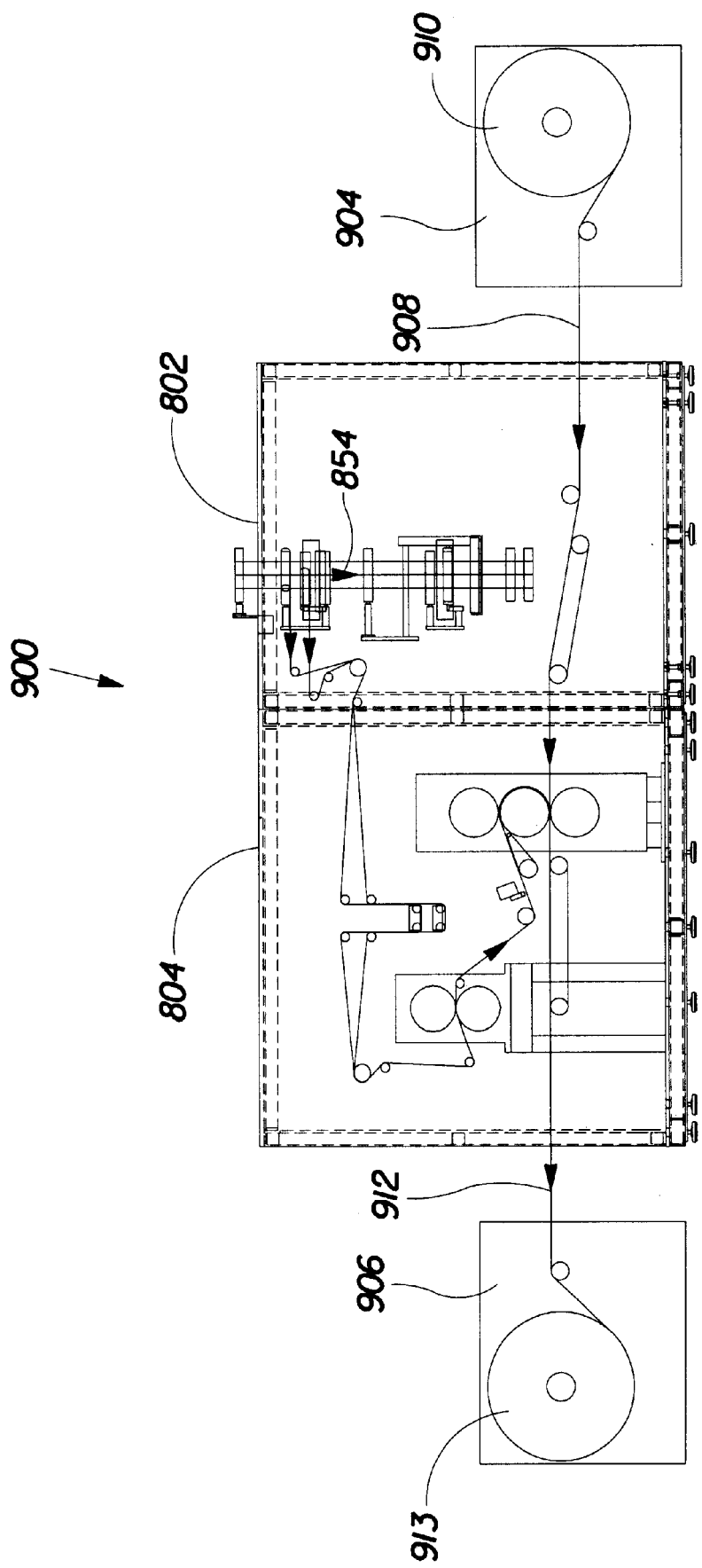
FIG. 23 is a simplified front view from the operator side of a standalone test stand operation.

The central operator interface 920 shown in FIG. 25 and the first and second operator interfaces 1070 and 1072, respectively, may display for the operator the messages concerning malfunctioning of the manufacturing system such as alarm messages. Some examples of alarm messages may be a number of product rejects, a tissue break, an above tolerance torque on a servo motor, a misalignment of a component, an above tolerance temperature, etc. The alarm messages for a group of one or more modules may be displayed on a local operator interface and/or on a central operator interface. As shown in FIG. 23, for example, the alarm messages for the first group of module(s) 1078 may be displayed on the first operator interface 1070, and the alarm messages for the second group of module(s) 1080 may be displayed on the second operator interface 1072. However, the central operator interface 920 may display the alarm messages related to both group of module(s) 1078 and 1080. In one embodiment, the alarm messages may be stored in the central logic controller 928 of the central computer 336.

The embodiment shown in FIG. 25, for example, may utilize the following commercial hardware: the master motion/drive reference 924 may be an Encoder Signal Reference Simulator (ESRS) manufactured by Rockwell International; the motion/drive control signal converter transmitter 926 may be an ALEC-4100 Axislink Encoder Converter manufactured by Rockwell; the central logic controller 1114 may be 1785-L40C PLC-5 manufactured by Rockwell; the motors 1073, 1074 and 1076 may be 1326 Servo Motors manufactured by Rockwell; the motion/drive controllers 1062 and 1064 may be 1394-SJT10-T-RL controllers manufactured by Rockwell; the local logic controllers 1066 and 1068 may be 1785-L40C15 PLC-5 Processors manufactured by Rockwell; the local operator interfaces 1070 and 1072 may be a 1585THX+1242 manufactured by IDT Cutler Hammer of Ohio; the central main operator interface 920 may be a D735SVPR64DWNT manufactured by IDT Cutler Hammer of Ohio.

Standalone Operation

One or more modules of the present invention may be operable off-line in a standalone mode. FIG. 23, for example, illustrates a two-module group 900 being used off-line in a standalone mode. The modules may be operated off-line in order to develop product upgrades in which the operational units of the group of modules 900 may be modified until the portion of the product being upgraded is manufactured as desired. The modules may also be run off-line to test their operation before they are installed in a converting line. Alternatively, the group of modules 900 may be used as a standalone production center for producing components of a product off-line. In one embodiment, a web material 908 may be a product web that includes all the portions of a finished product except the portion(s) being assembled by the group of module(s) 900 being run in a standalone mode. The rewind device 906 may create a roll of the combined web 913 including the portion assembled by the group of modules 900.

In one particular example, the group of modules 900 may be supported by a docking station for supplying power distribution, safety systems, compressed air, vacuum, glycol, adhesive(s) and other utilities as needed. One or more modules of the group of modules 900 may be connected to the docking station similarly as they would have been connected on a manufacturing line and as shown in FIGS. 15 and 16, and described above.

During standalone mode operation, a local controller may control the operation of the operational units in the group. The local controller may independently synchronize and coordinate the operation of the motors and logical devices in the group, or may receive a reference signal from an external source that may be used to simulate the reference signal described above that it would receive in the flexible manufacturing system.

Use of individual modules as "test stands" for a portion of a product may eliminate a step from typical product upgrades. For example, a standalone operation of one or more modules that may be inserted into a prototype line may allow for combining the steps of constructing a high speed test stand that may manufacture the portion of the product being upgraded in isolation at high speeds in order to test the feasibility of high speed manufacturing and constructing a prototype line that is able to make complete prototype products at high speeds of a typical product upgrade development. Thus, once built and tested, the standalone modules that function as the high speed test stand may be inserted into a prototype line and products including the newly developed product may be assembled at high speeds without having to construct or reconstruct a complete prototype line. Further, the standalone module(s) may first be utilized as a preliminary machine production unit that may manufacture the portion of the product being upgraded and/or the entire product incorporating the upgrade in order to determine product and process feasibility, then as a high speed test stand and finally inserted into a high speed prototype line. Also, once the product upgrade has been successfully produced on a high speed prototype line, the module(s), or substantially similar module(s), may be inserted into one or more production lines. Even further, where multiple production lines are designed in accordance with the present invention, product upgrades may be easily rolled out over multiple production lines because substantially similar or identical modules that have been tested on a pilot line or another production line may be easily inserted into multiple production lines after the testing and debugging of the modules have been completed on other lines. Thus, the down time of each production line may be drastically reduced.

Product Upgrade

Many product upgrades seek to enhance the performance and/or the aesthetics of the product or decrease the cost of the product by changing one or more particular portions of a product. A diaper product, for example, may be upgraded from a single cuff diaper having a gasketing cuff 536 to a multiple cuff diaper by adding a barrier cuff 538. Alternatively, a product line may manufacture multiple different products on the same line by changing one or more portions of a product. A line may manufacture a unibody design diaper, for example, in which the side panels are created by cutting notches in the web to create leg openings of a diaper. That same line may also manufacture a multi-piece design diaper such as the diaper 550 shown in FIG. 33 in which the side panel portion of the unibody design diaper 500 is replaced by prefabricated back ears and front ears that may be produced off-line at a significant cost savings.

If the equipment that manufactures, attaches or assembles a complete or substantially all of portion of a product is physically co-located and commonly controlled, changing the production line to alter, replace or remove that portion from a product may significantly reduce the time and costs required for off-line development, testing and line changeover efforts. In one particular embodiment, for example, each operational unit that is, or substantially all the operational units that are, used to manufacture, attach or assemble a particular portion of a product may be housed in one or more modules dedicated to that portion. These modules may be arranged adjacent to each other in the manufacturing line and may even be commonly controlled.

As described above, a flexible manufacturing system of the present invention may include a group of one or more modules that house substantially all of the equipment that manufactures a particular portion of a product. In one particular embodiment, for example, the equipment in the one or more modules may be controlled directly by a local control function. In this embodiment, the local control function may utilize a reference signal provided by a global control function to coordinate the operation of at least one motor and/or one logical device of the group of one or more modules to the remainder of the flexible manufacturing line. In a particularly preferred variation of this embodiment, the flexible manufacturing system may include at least two independent groups of one or more modules that manufacture different portions of a product. In this embodiment, each group may include a local control function that is adapted to directly control motors and logical devices for that particular group and to synchronize or coordinate those motors and logical devices to the rest of the flexible manufacturing system by utilizing one or more reference signals. In another variation, the local control function of each group of one or more modules may be adapted to directly control the motors and logical devices for that group of one or more modules in either a standalone mode or in the event that the group of one or more modules is integrated into an overall converting line.

Adding/Replacing Module

Figure 24:
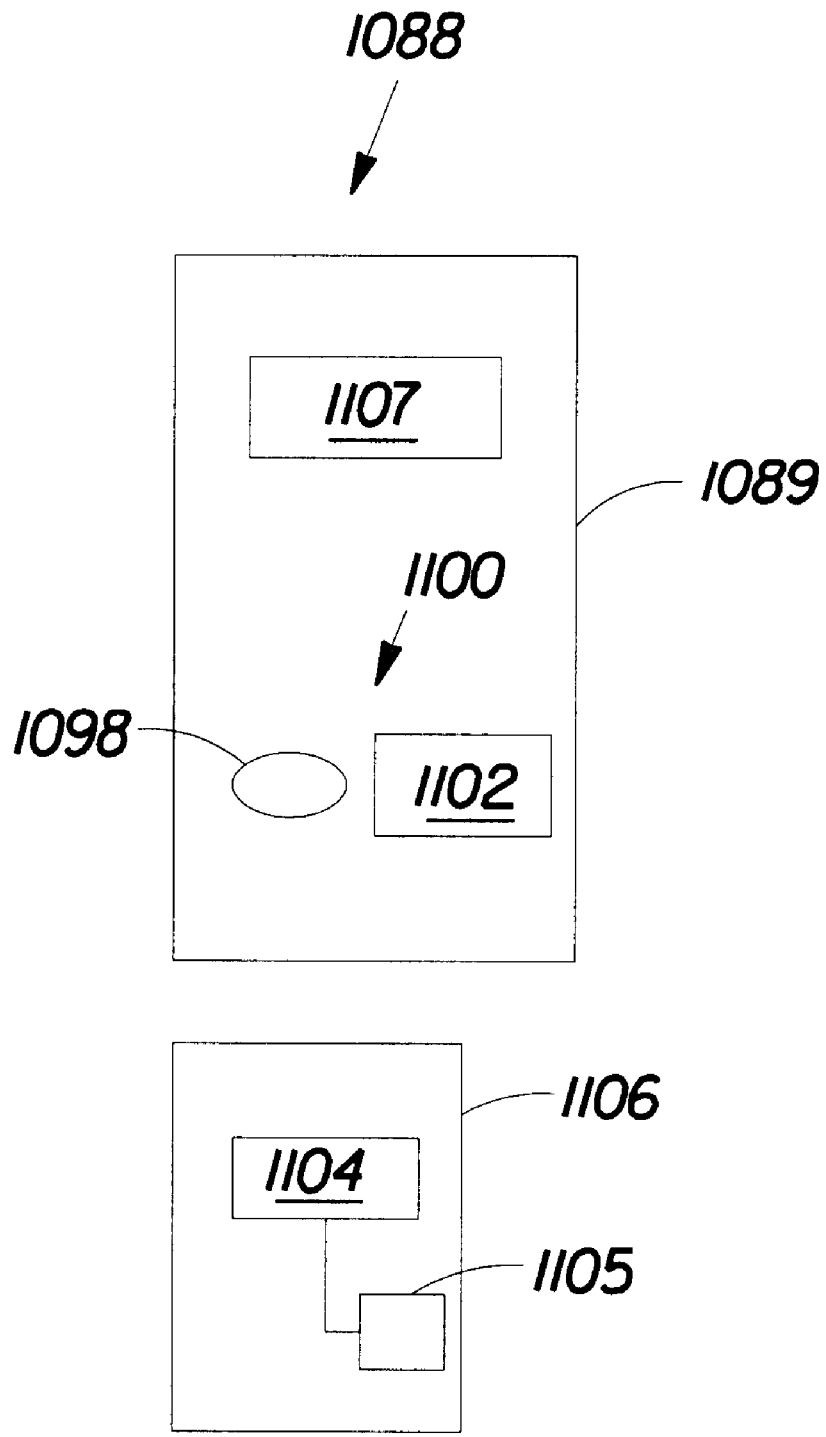
FIG. 24 is a block diagram of a standalone operation or of a module that may be added to a manufacturing line.

FIG. 24 illustrates a module 1089 and a local controller 1106 that may be adapted to be an addition to the flexible manufacturing system and/or a substitution of one or more modules of the flexible manufacturing system. In one embodiment, the module 1089 may be configured to be capable of producing a new, alternative or modified portion of a product. In this embodiment, the module 1089 may be inserted into the flexible manufacturing system in order to allow the line to produce a different product or a different variation of a product (e.g., a different size). The module 1089 may include at least one operational unit 1100 which may include at least one control device 1102 and/or at least one motor 1098. The local controller 1106 may also include at least one local motion/drive controller 1104 and at least one local logic controller 1105. Further, the module 1089 may include at least one local operator interface 1107.

In one particular embodiment, when one or more modules are added to or removed from a flexible manufacturing line of the present invention, the change in the line preferably does not affect the operation of upstream or downstream modules. In order to ensure that the change in the line does not affect the product pitch of operational units housed in modules located downstream of the changed flexible manufacturing line, the change in a web length or product path of the flexible manufacturing system due to the change is preferably equal to an integer number of product pitch lengths. Thus, the change in the flexible manufacturing system may be transparent to any downstream operations that are sensitive to product pitch. Although the web length or product path length in the group of module(s) inserted or removed is preferably equal to an integer number of product pitch lengths, the web length or product path length in the group of module(s) being inserted or removed may not be an exact integer number of product pitch lengths. For example, the net change in web length or product path length may be equal to an integer number of product pitch lengths where one or more modules are removed and one or more modules are added to the line or if the web path length is adjusted in one or more other modules remaining in the line, such as an adjacent module.

When one or more modules are removed from or added to the manufacturing system, the control files concerning the removed or added module(s) section may also be removed from or added to the central computer 336. See e.g., FIG. 25. Alternatively, the central computer may contain the control files for various module configurations and when the central computer is informed, such as by an operator input, a software flag from the local controller or stored within the central computer itself, the central computer may look up the correct control file corresponding to that module configuration. The term "updating control files" may include both the removal and/or the update of the control files, or may include informing the central computer of the module(s) that are currently connected to the manufacturing system. The control files may be updated manually or automatically. Manually updating control files may involve, for example, connecting a personal computer 1050 (see e.g., FIG. 25), having logic control software, to the logic control sub-network link 1052 for removing the control files stored in the central logic controller 928 or for adding new control files into the central logic controller 928. Automatically updating control files may involve having the central logic controller 928 read control files in every local controller of the flexible manufacturing system via the logic control sub-network links 1052 and 1056 after an initialization signal has been provided by the operator from the main operator interface 920 (see e.g., FIG. 25) or from the local operator interface 1107 (See e.g., FIG. 24).

Safety Lockout

The manufacturing system of this invention includes a safety lockout system for shutting off the electrical power supply from the manufacturing system and for preventing an inadvertent motion of the manufacturing system during the shutdown. The safety lockout system may be any lockout system used in the art of machine control, however, in one particular embodiment of the invention, the safety lockout system may be an 800 ampere rated lockout system from Moeller Electric Company of Bonn, Germany. This safety lockout system enables having a safety disconnect in every module connected to a 24 volts control cable instead of running heavy power cables (for example, 400 volts) between the modules. The latter option would be more costly and take more physical space. The capability of having a power disconnect at every module provides safety and convenience for the operators and maintenance personnel.

Figure 31:
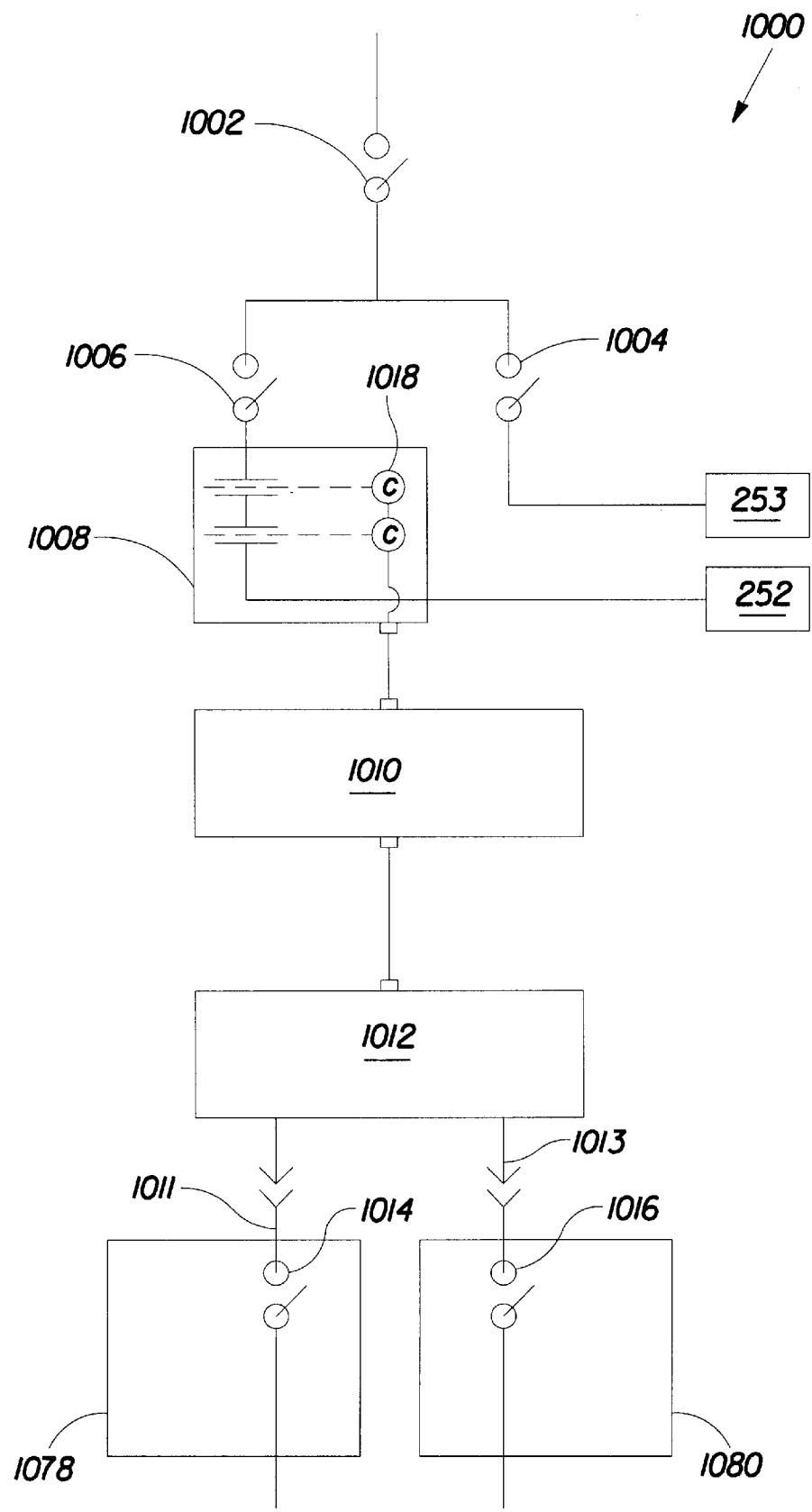
FIG. 31 is a block diagram of a safety lockout system.

FIG. 31 shows a block diagram of one embodiment of a safety lockout system 1000. The safety lockout system 1000 preferably includes a manual main switch 1002, a manual auxiliary bus switch 1004, a manual motion bus switch 1006, motion bus contactor unit 1008, a control unit 1010, a distributor unit 1012, and one or more safety lockout switches 1014, 1016, etc., each providing electric power to a supporting module. The motion bus contactor unit 1008 may provide electric power to a motion bus 252. The power unit 1000 preferably includes contactors 1018 for interrupting the power to the motion bus 252. A manual switch 1004 may serve for interrupting the power to an auxiliary bus 253. Alternatively, the auxiliary bus 253 may include a similar contactor scheme as described above with respect to the motion bus 252. The control unit 1010 may provide a redundant safety monitoring and interlock. The distributor unit 1012 preferably monitors multiple safety switches 1014, 1016, etc. and when one or more of the multiple safety switches is open, the distributor unit 1012 sends a signal to the control unit 1010 informing the control unit 1012 that one or more of the safety switches is open. The control unit 1010, then de-energizes the redundant contactors 1007 to remove power from the motion bus 252.

FIG. 28 shows a preferred embodiment of a power distribution center panel 328 that forms a part of the safety lockout system 1000. The power distribution center panel 328 may include a control unit 1030, a distribution unit 1032, a motion bus contactor unit 1034, a manual motion bus switch 1036, a manual auxiliary bus switch 1038, a manual packing switch 1040, and a manual main switch 1042. Alternatively, the distribution unit 1032 may also be distributed throughout the production line. This may reduce the number and length of cables that need to be run from the individual safety lockout switches 1014, 1016,. etc. to the power distribution center panel 328 shown in FIG. 28.

Panel Support Structure

FIGS. 13, 15, 17 and 18 show a panel support structure 240 that may support a fluid utility system 302, an electrical power system 304, standard control panels 370, standard main control panels 371, standard auxiliary control panels 374, standard adhesive control panels 960, source material, etc. to provide more operating floor space and improved access to the converting line. The panel support structure 240 may be about the same length as the manufacturing line, and may be located immediately adjacent to the drive side of the line. The panel support structure 240 may be prefabricated in lengths that can be easily shipped to a plant site in standard shipping containers and assembled quickly on the plant site by using commercial hardware as shown in FIGS.

17–22. The prefabricated sections may include one or more platform 242, support columns 244, stairs 246, safety hand rails 248, wireways 249 and 256, two power distribution bus ducts 252 and 253, utility header supports 254, and cross braces 258. The platforms 242 may be of standard lengths, such as about 3.5 and/or about 4 meters.

Figure 18:
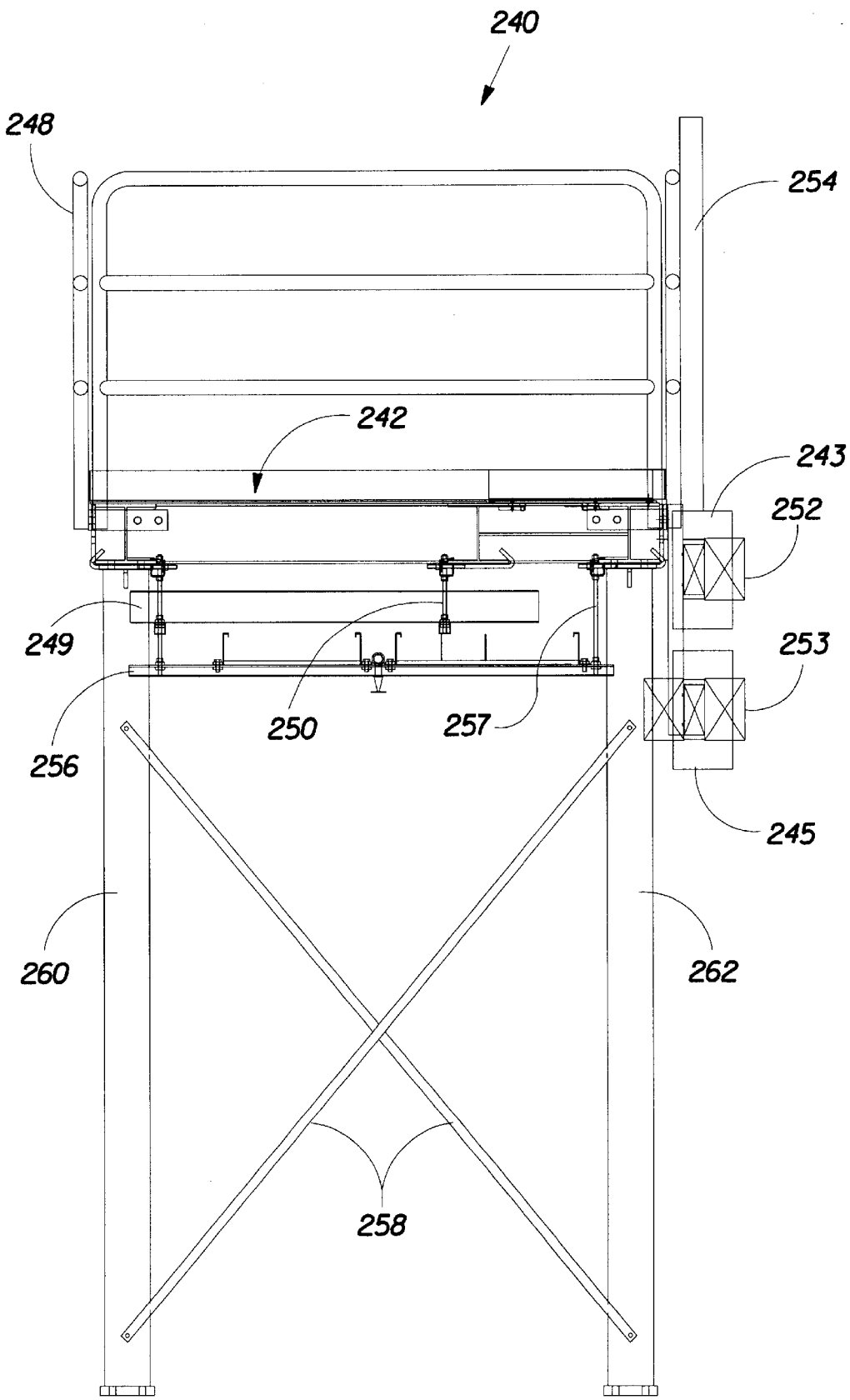
FIG. 18 is a side view of a panel support structure shown in FIG. 17.
Figure 21:
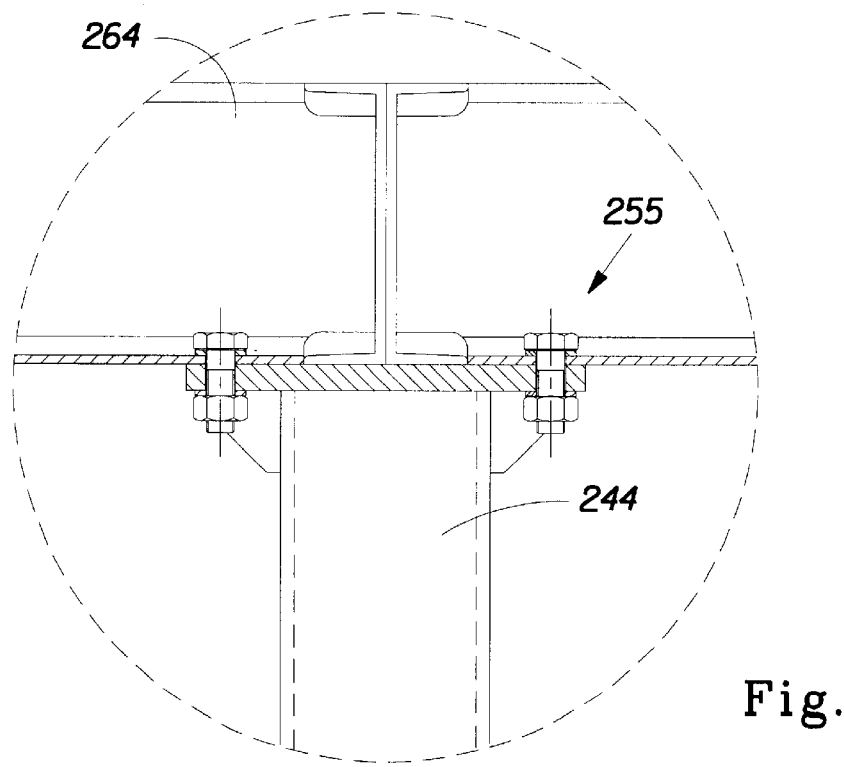
FIG. 21 is an enlarged view of area 28 shown in FIG. 17.
Figure 22:
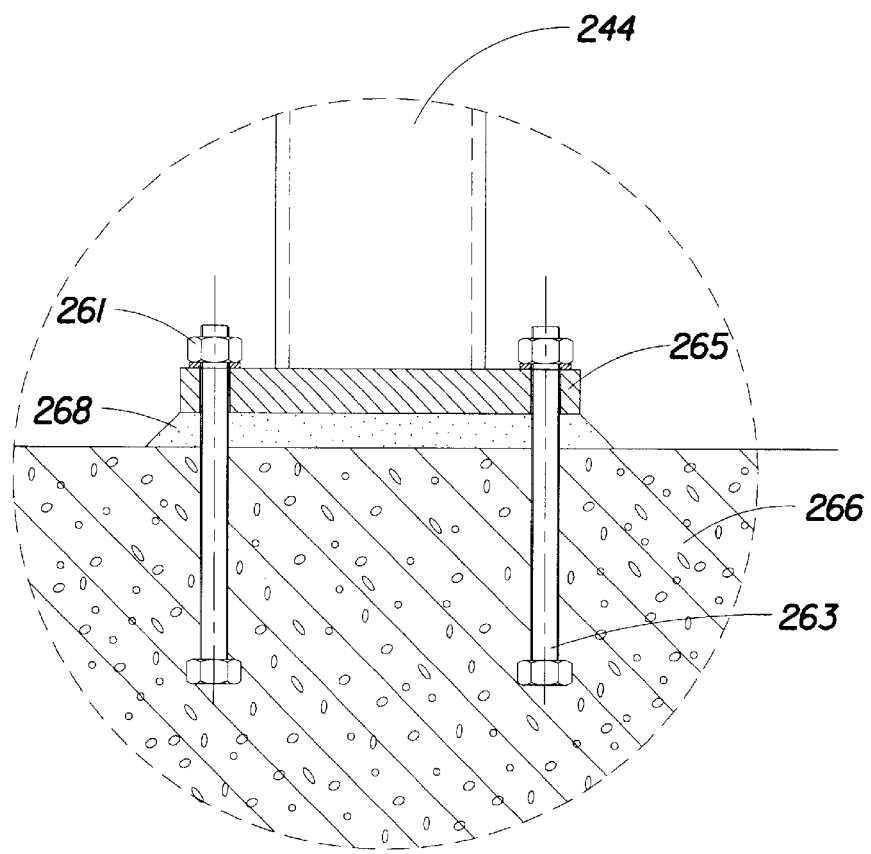
FIG. 22 is an enlarged view of area 29 shown in FIG. 17.

There are preferably two rows of columns 260 and 262 supporting the panel support structure 240 as shown in FIG. 18. The row 260 is located along the edge of the panel support structure 240 immediately adjacent to the modules and the row 262 is located along the side distant from the modules. The support columns are preferably of a moveable design and are preferably located adjacent to the connecting line between the modules. This location creates a convenient access to the drive side of the modules by allowing the drive side guard doors to be open a full 90 degrees without obstruction. In the event a change such as a product upgrade or product change for the manufacturing line results in a change of a module length, and this results in a column blocking access to one or more modules, it may be desirable to relocate the column to the connecting line location between two modules. To accomplish this quickly, the platform beam 264 to which the support column 244 (FIG. 21) attaches is preferably pre-drilled with a series of holes that s allow it to be reattached without further modification to the platform beam 264 or the column 244. The hole pattern may be repeated incrementally in a distance equal to the incremental difference between different size modules used in the converting line. For example, if the modules of a particular converting line are 1.0, 1.5, 2.0 and 2.5 meters in width, the hole patterns may be repeated every 0.5 meters along the panel support structure.

Control panels, such as the standard main control panels 370, the standard auxiliary control panels 374 and the standard adhesive panels 960, may be located on the panel support structure 240 and may be attached to the panel support structure 240 with clamps that eliminate a need to drill holes in the panel support structure 240 and allow easy installation and removal of the panels.

As shown in FIGS. 15 and 16, the utility header supports 254 may be used to support piping for compressed air, vacuum, glycol, etc. directed to parts of the manufacturing line where they are needed. Having them supported independently from the modules and from the control panels enhances the ability to make rapid changes of the modules of the manufacturing line.

Figure 19:
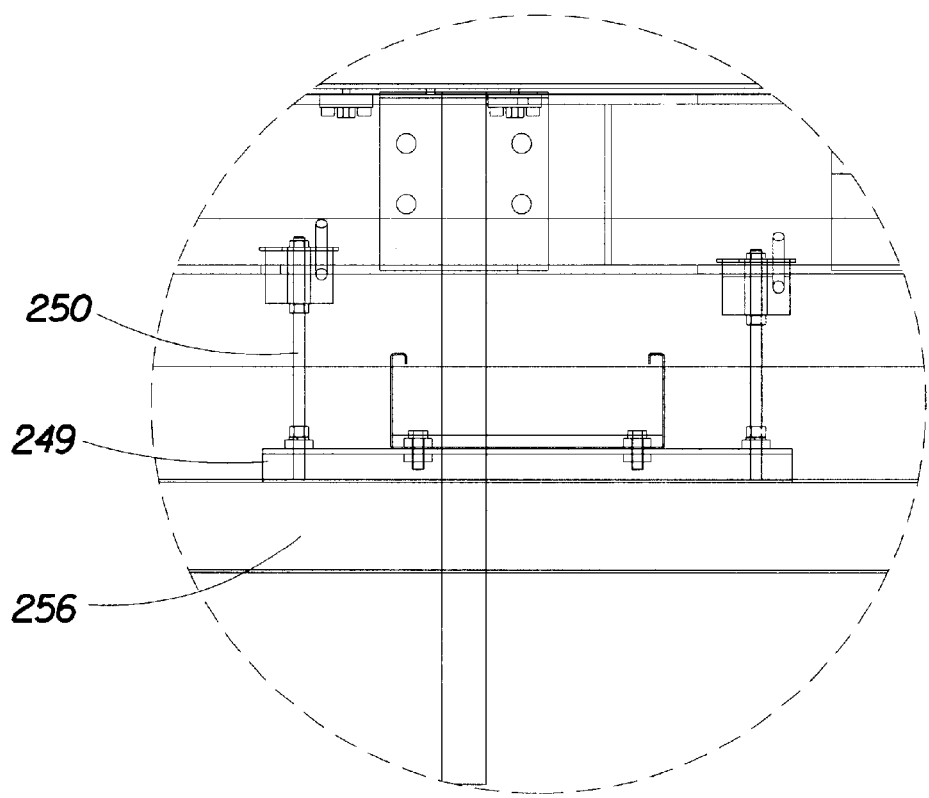
FIG. 19 is an enlarged view of area 26 shown in FIG. 17.
Figure 20:
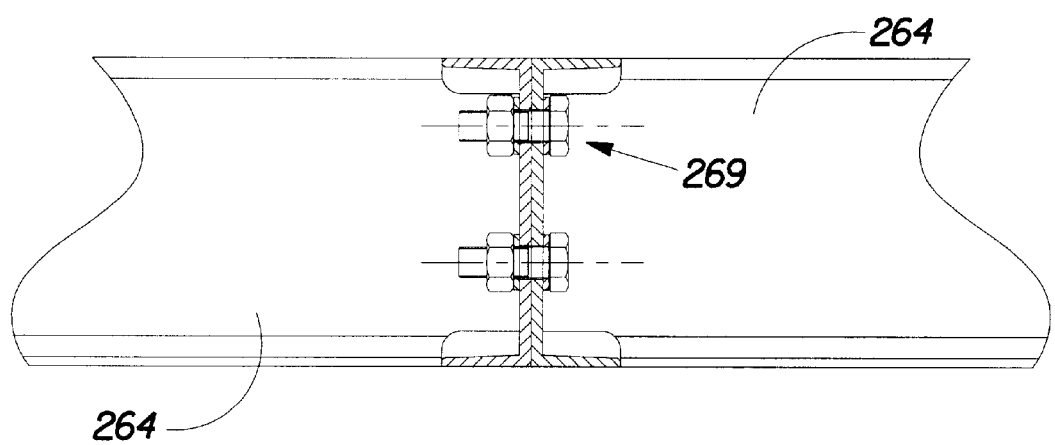
FIG. 20 is an enlarged view of a connection of two platform beams of the panel support structure shown in FIG. 17.

The wireways 249 and 256 may be used to support electrical control cables, power cables, adhesive hoses, etc. that may be run to a particular module as shown in FIGS. 15, 18 and 19. This approach may save time during the initial installation and whenever a module is removed, added or replaced for an upgrade because operators are not required to disturb or re-pull unrelated cables or hoses.

Multiple power distribution buses, such as the motion power distribution bus 252 and the auxiliary power distribution bus 253, may be mounted independently to the panel support structure 240 These buses may be located near the base of the control panels and run parallel to the manufacturing line.

FIG. 15 illustrates a module 300 positioned adjacent to the panel support structure 240 and also connections of the module 300 to a fluid utility system 302 and to an electric power system 304. The module 300 may be located adjacent to the panel support structure 240 under a header support 254. The header support 254 is attached to the panel support structure 240 and supports the fluid utility system 302 which may include headers attached to the header support 254 such as the following: a compressed air header 306, a low vacuum header 308, a house cleaning vacuum header 310, a high vacuum header 312, a glycol supply header 314 and a glycol return header 316. The headers may include separate sections of headers connected together to form a continuous header system generally along the full length of the manufacturing line. The headers may be connected via pipe, ducts, hoses or tubes (also called "drops") to quick disconnects located immediately above the module 300 such as shown in FIGS. 15 and 16. The quick disconnects may include a compressed air quick disconnect 324, a low vacuum quick disconnect 318, a house cleaning vacuum quick disconnect 322, a high vacuum quick disconnect 320, and two glycol quick disconnects 326. The quick disconnects may be operated without tools and shorten the time needed to connect and disconnect the utilities. To minimize the number of connections, it may be preferable to have no more than one entry per utility for each module. From that entry, a particular fluid utility is routed inside the module to desired destinations. If a particular utility is not required for a particular module, the header of this utility may be closed off such as with an end cap or a valve.

As shown in FIG. 15, the electrical power may be supplied from a power distribution center 328 to a motion bus 252 and an auxiliary bus 253 via power cables 330 and 332, respectively. Both the motion bus 252 and the auxiliary bus 253 may be attached to the panel support structure 240. The motion bus 252 may be connected to at least one motor 280 located in the module 300 via a motion/drive controller 334. The motion/drive controller 334 may be connected to the motion bus 252 via a motion power cable 333 and a quick disconnect 337 and to the motor 280 via power and feedback cables 339 and 342, which are preferably connected via a quick disconnect 344 located immediately above the module 300. The motion/drive controller 334 may be also connected to a central computer 336 via a control motor cable 338. The auxiliary bus 253 may be connected to at least one logic controller 340 via a logic power cable 341 and a quick disconnect 345. The logic controller 340 may be connected to an electrical junction bus 346 as shown in FIG. 16 by a remote local network cable 348 and a quick disconnect 350. The logic controller 340 may be also connected to the central computer 336 via a logic control network cable 352. An operator interface 354 may be attached to a guard door 356 and connected to the electrical junction box 346 by a remote local network cable 358. A safety lockout switch 360 may be attached to a guard door 356 below the operator interface 354. The safety lockout switch 360 may be connected to the power distribution center 328 via a safety lockout switch cable 362 and a quick disconnect 364. The remote local network cable 348, the safety lockout switch cable 362, and the power and feedback cables 339 and 342 may be extended through a wireway 249, which may be attached to the panel support structure 240. The wireway 249 may be dedicated to the module 300 or to a particular group of modules in order to prevent the cables connecting the module 300 or the particular group of modules from being intermingled with cables for other modules. This approach may save time during the initial installation and whenever a module or group of modules is removed, added or replaced in the manufacturing system.

Both the motion controller 334 and the logic controller 340 may be located in a control panel 370 described in more detail below. The control panel 370 may be located above the floor on the panel support structure 240 and adjacent to the module 300. The front 372 of the control panel 370 may be facing the module 300. This layout creates a direct line of sight between an electrician working at the control panel 370 on the panel support structure 240 and an operator on the floor facing the module 300. This may also allow for better communication and may lead to shorter trouble shooting times and a safer operating environment. More than one control panel may be used for a particular module or group of modules if necessary to house the required control equipment for that particular module or group of modules.

If a module includes at least one adhesive applicator 380, as shown in FIG. 30, for example, then the module may also be provided with an adhesive junction box 382 which may be located, for example, on a right top side of the module 300. The adhesive applicator 380 may receive adhesive from an adhesive tank 384 via a pump 386, a supply hose 388, a remote meter applicator 390, and a hose 392. A module may include one or more adhesive applicators supplied with one or more adhesives. Control of these adhesive applicators, for example, may be provided by a local controller housed in a standard main control panel 371 and a standard adhesive control panel 960. The standard adhesive control panel 960 may be located on the panel support structure 240 adjacent to the standard main control panel 371.

Methods Of Line Change

The manufacturing system of this invention may provide flexibility for removing one or more modules from the manufacturing system and/or adding one or more modules to the manufacturing system. For example, if there is a need to change a product design that involves a change in a design of a particular portion of a product, a group of module(s) of the manufacturing system producing that portion of the product may be removed from the manufacturing system and another group of module(s) adapted for producing the new portion of the product may be used to replace the removed group of module(s). The added group of module(s) may physically fit or not fit in the space vacated by the removed group. If the added group physically fits into the space, then no change in the position of adjacent module(s) may be necessary. However, if the added group of module(s) physically does not fit into the space, then a change in position of adjacent module(s) may be necessary. Further, if there is a need to add a new portion of a product, a new group of module(s) may be added to the manufacturing system. Adding a new group of module(s) may or may not involve a change in position of adjacent module(s).

Referring to FIGS. 1–6, 11–12, 15, 16 and 31, removing a module from a manufacturing line may involve all or some of the following steps (not necessarily in the order listed below):

1) Lock out the motion bus 252, the auxiliary bus 253, and the safety lockout switch 360.
2) Disconnect the power and feedback cables 342 such as via the quick disconnects 344.
3) Disconnect the logic control network cable 348 from the electrical main junction box 346 such as via the quick disconnect 350.
4) Disconnect the house cleaning vacuum such as via quick disconnect 322.
5) Disconnect the low vacuum such as via quick disconnect 318.
6) Disconnect the high vacuum such as via quick disconnect 320.
7) Disconnect the glycol supply and return such as via quick disconnects 326.
8) Disconnect the compressed air supply such as via quick disconnect 324.
9) Disconnect and remove the adhesive supply hose(s) 388.
10) Disconnect and remove the safety lockout switch cable 362 from the power and distribution center panel 328 such as via a quick disconnect 364.
11) Set up lifting mechanism manifold 130 and thread air lines 132 to the module.
12) Insert lifting mechanisms 30 into regions 22 under the module.
13) Remove bolts and pins 38, spacers 36, and wedges 32 and 34 from the module.
14) Measure and record the height of feet 26 on the module from the floor to the bottom of the horizontal plate 16.
15) Secure the module. For example, a person may be placed on the operator side and on the drive side of the module.
16) Activate the lifting mechanism and remove the module from the line. For example, the lifting mechanisms 30 may be inflated, and the module may be slowly pushed out of the line.
17) Move the module out of the way and lower the module. The lifting mechanism 30, for example, may be slowly deflated.

Referring to FIGS. 1–6, 11–12, 15, 16 and 31, inserting a module into a manufacturing line may, for example, involve all or some of the following steps (not necessarily in the order listed below):

1) Lock out the module's motion bus 252, the auxiliary bus 253, and the safety lockout switch 360.
2) Adjust the height of the feet of the module being inserted to the height of the feet 26 of the replaced module.
3) Insert lifting mechanisms 30 into regions 22 under the module.
4) Secure the module. For example, a person may be placed on the operator side and on the drive side of the module.
5) Activate the lifting mechanism. For example, the lifting mechanisms 30 may be inflated.
6) Guide the module into an aligned position on the manufacturing line.
7) Lower the lifting mechanism. For example, the lifting mechanisms 30 may be deflated and removed.
8) Adjust the feet 26 of the module to ensure that the vertical plates 10 and 12 of the module being inserted and of the adjacent module(s) are parallel and that the modules are at the same elevation.
9) Insert spacers 36 and wedges 32 and 34 and secure the module with bolts and pins 38.
10) Connect the house cleaning vacuum such as via quick disconnect 322.
11) Connect the low vacuum such as via quick disconnect 318.
12) Connect the high vacuum such as via quick disconnect 320.
13) Connect the glycol supply and return such as via quick disconnects 326.
14) Connect the compressed air supply such as via quick disconnect 324.
15) Connect the adhesive supply hose(s) 388.
16) Connect the safety lockout switch cable 362 to the power distribution center 328 such as via a quick disconnect 364.
17) Connect the logic control network cable 348 to the electrical main junction box 346 such as via a quick disconnect 350.

18) Connect the power and feedback cable 342 such as via the quick disconnects 344.
19) Unlock the motion bus 252, the auxiliary bus 253, and the safety lockout switch 360.
20) Load module software into the motion controller 334 and the logic controller 340.
21) Push the start button on the operator interface 354 or the main operator interface 630.

This may automatically home the drives.

Standard control panels such as standard control panels 370 shown in FIG. 27 may be reconfigured to perform as a control panel for a different group of one or more modules, or may be added to, replaced in or removed from a flexible manufacturing system of the present invention. If a group of one or more modules is replaced by another group of one or more modules, often the standard control panels for the group that is being removed may be reconfigured as control panels for the new group. In this case, software and/or hardware in the standard control panels may be replaced or reconfigured in order to control the operation of the new group of one or more modules. Alternatively, if a new group is inserted into the flexible manufacturing system and no spares already exist along the line that may be configured as control panels for that group, one or more new standard control panels such as a standard main control panel 370N, a standard auxiliary panel 374N and/or a standard adhesive panel 960N may be installed to support the new group of one or more modules such as shown in FIGS. 27 and 29. New standard control panel(s) may also need to be installed in different locations along the flexible manufacturing system than the panel(s) being replaced. If it is necessary to remove an existing standard control panel and to install a new standard control panel, all or some of the following steps, for example, may be performed (not necessarily in the order listed below):

1) Lock out the module's motion bus 252, auxiliary bus 253 and safety lockout switch 360.
2) Disconnect the electrical power cable 333 from the motion bus 252 such as via a quick disconnect 337.
3) Disconnect the electrical power cable 341 from the auxiliary bus 253 such as via a quick disconnect 345.
4) Disconnect the remote local network cable 348 from the electrical main junction box 346 such as via a quick disconnect 350.
5) Disconnect the control motion cable 338 from the motion controller 334 inside the standard control panel 370.
6) Disconnect the logic control network cable 352 from the logic controller 340 inside the standard control panel 370.
7) Disconnect the power and feedback cable 342 such as via the quick disconnect 344.
8) Remove the standard control panel 370.
9) Install a new standard electric panel 370N.
10) Connect the power and feedback cable 342 such as via the quick disconnect 344.
11) Connect the logic control network cable 352 from the logic controller 340 inside the new standard control panel 370N.
12) Connect the control motion cable 338 from the motion controller 334 inside the new standard control panel 370N.
13) Connect the remote local network cable 348 from the electrical main junction box 346 such as via the quick disconnect 350.
14) Connect the electrical power cable 341 from the auxiliary bus 253 such as via the quick disconnect 345.
15) Connect the electrical power cable 333 from the motion bus 252 such as via the quick disconnect 337.
16) Unlock the motion bus 252, the auxiliary bus 253, and the safety lockout switch 360.
17) Load module software into the motion controller 334 and the logic controller 340 of the new standard control panel 370N.
18) Push the start button on the operator interface 354 or the main operator interface 920.

This may automatically home the drives.

If an existing standard control panel is to be removed but a new standard control panel is not to be added, steps 1–8 may be sufficient. Alternatively, if a new standard control panel is to be added, but no existing standard control panels are to be removed, steps 9–18 may be sufficient.

When replacing a module with a module that has a different length than the original module or when modules are rearranged and the location of module to module connections are changed, the panel support structure 240 shown in FIGS. 17–22 may require reconfiguration of the panel support structure 240. The reconfiguration may involve changing the location of one or more columns 244, changing the location of the wireway 249, and/or relocating or adding the header support 254 shown in FIG. 15.

Changing a location of a column may, for example, involve all or some of the following steps (not necessarily in the order listed below):

1) Before removing the column to be removed or replaced, position a new column under the panel support structure 240 in the new location.
2) Align the new column with the correct pre-drilled holes in the beam 264.
3) Place a shim, such as a 25 mm thick shim, under the new column.
4) Bolt the top of the new column to the beam with bolts 255.
5) Drill holes, such as the four holes shown, into the floor.
6) Insert bolts 263, such as adhesive threaded rod anchor bolts, through the base plate 265 and into the four holes in the floor.
7) Grout under the new column and secure nuts 261 onto the base plate 265.
8) Tighten the bolts 255 at the top of the new column.

Once the new column is secured in place, it may be safe to remove the old column causing to allow free movement of the doors of new module. The removal of the old column may, for example, involve all or a portion of the following steps (not necessarily in the order listed below):

1) Remove the grout 268 from under the old column.
2) Cut the four bolts 263 attaching the old column to the floor.
3) Unscrew the bolts 255 at the top of the old column from the beam 264 and remove the old column.

EXAMPLE

In one embodiment of the present invention, the flexible manufacturing system may comprise a converting line that may manufacture absorbent articles such as diapers, adult incontinence articles, feminine hygiene tampons, sanitary napkins, wipes, mops, bandages, etc. As used in this application, the term "absorbent article" refers to devices which absorb and contain body exudates, and more specifically, refers to devices that are placed against or in proximity to the body of the wearer to absorb and contain the various exudates discharged from the body. The term "disposable" is used to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.)

Figure 32:
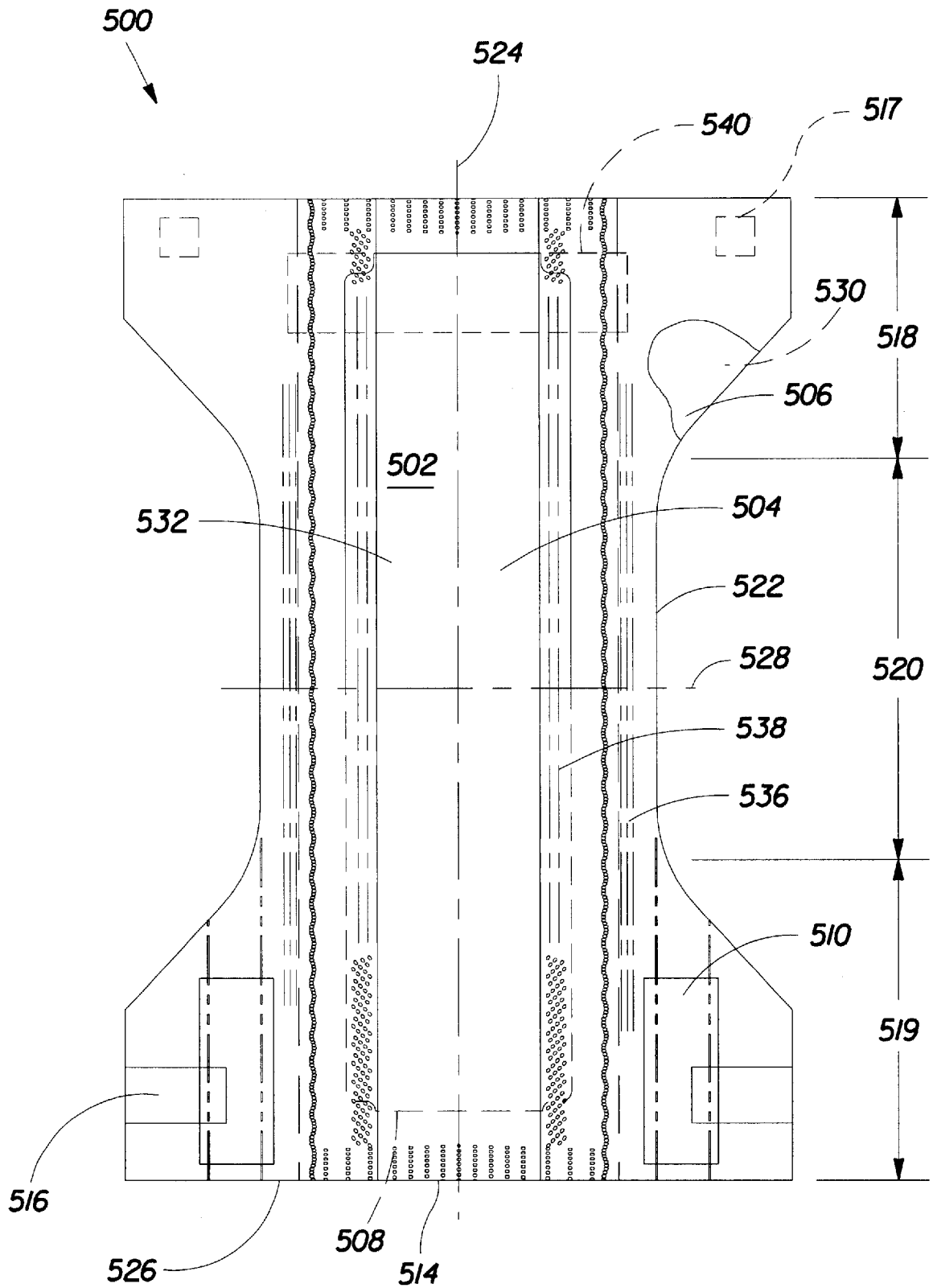
FIG. 32 is a plan view of a disposable diaper which could be manufactured using the present invention, the diaper having portions cut away to reveal the underlying structure of the diaper.

For illustrative purposes, the flexible manufacturing system of the present invention may be described comprise a converting line that manufactures disposable diapers. The present invention, however, is not limited to a diaper converting line, but may be utilized in manufacturing many different types of disposable and durable products. The design, or construction, of the individual operational units within the flexible manufacturing system form no part of the present application, and, therefore, will not be described in great detail. The term "diaper" as used in this application refers to an absorbent article generally worn by infants and incontinent persons about the lower torso. FIG. 32 shows a plan view of a unibody diaper 500, which may be manufactured by a flexible manufacturing system of the present invention, in a flat-out state with portions of the structure being cut-away to more clearly show the construction of the diaper 500. The portion of the diaper 500 which faces the wearer is oriented towards the viewer. As shown in FIG. 32, the diaper 500 preferably comprises a liquid pervious topsheet 504; a liquid impervious backsheet 506; an absorbent core 508, which is preferably positioned between at least a portion of the topsheet 504 and the backsheet 506; side panels 510; gasketing leg cuffs 536; barrier leg cuffs 538; an elastic waist 514; a primary fastening system generally designated as 516; and a secondary fastener 517. Diaper 500 is shown in FIG. 32 to have a first waist region 518, a second waist region 519 opposed to the first waist region 518 and a crotch region 520 located between the first.waist region 518 and the second waist region 519. The periphery of the diaper 500 is defined by the outer edges of the diaper 500 in which the longitudinal edges 522 run generally parallel to a longitudinal centerline 524 of the diaper 500 and the end edges 526 run between the longitudinal edges 522 generally parallel to a lateral centerline 528 of the diaper 500.

A chassis 502 of the diaper 500 comprises the main body of the diaper 500. The chassis 502 comprises at least a portion of the absorbent core 508 and preferably an outer covering layer including the topsheet 504 and the backsheet 506. For unitary absorbent articles, the chassis 502 comprises the main structure of the diaper with other features added to form the composite diaper structure. While the topsheet 504, the backsheet 506, and the absorbent core 508 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article. With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The diaper 500 may also comprise side panels 510. The side panels 510 may be elastic or extensible to provide a more comfortable and contouring fit by initially conformably fitting the diaper 500 to the wearer and sustaining this fit throughout the time of wear well past when the diaper 500 has been loaded with exudates since the elasticized side panels 510 allow the sides of the diaper 500 to expand and contract. The side panels 510 may also provide more effective application of the diaper 500 because even if the diaperer pulls one elasticized side panel 510 farther than the other during application, the diaper 500 will "self-adjust" during wear.

Figure 33:
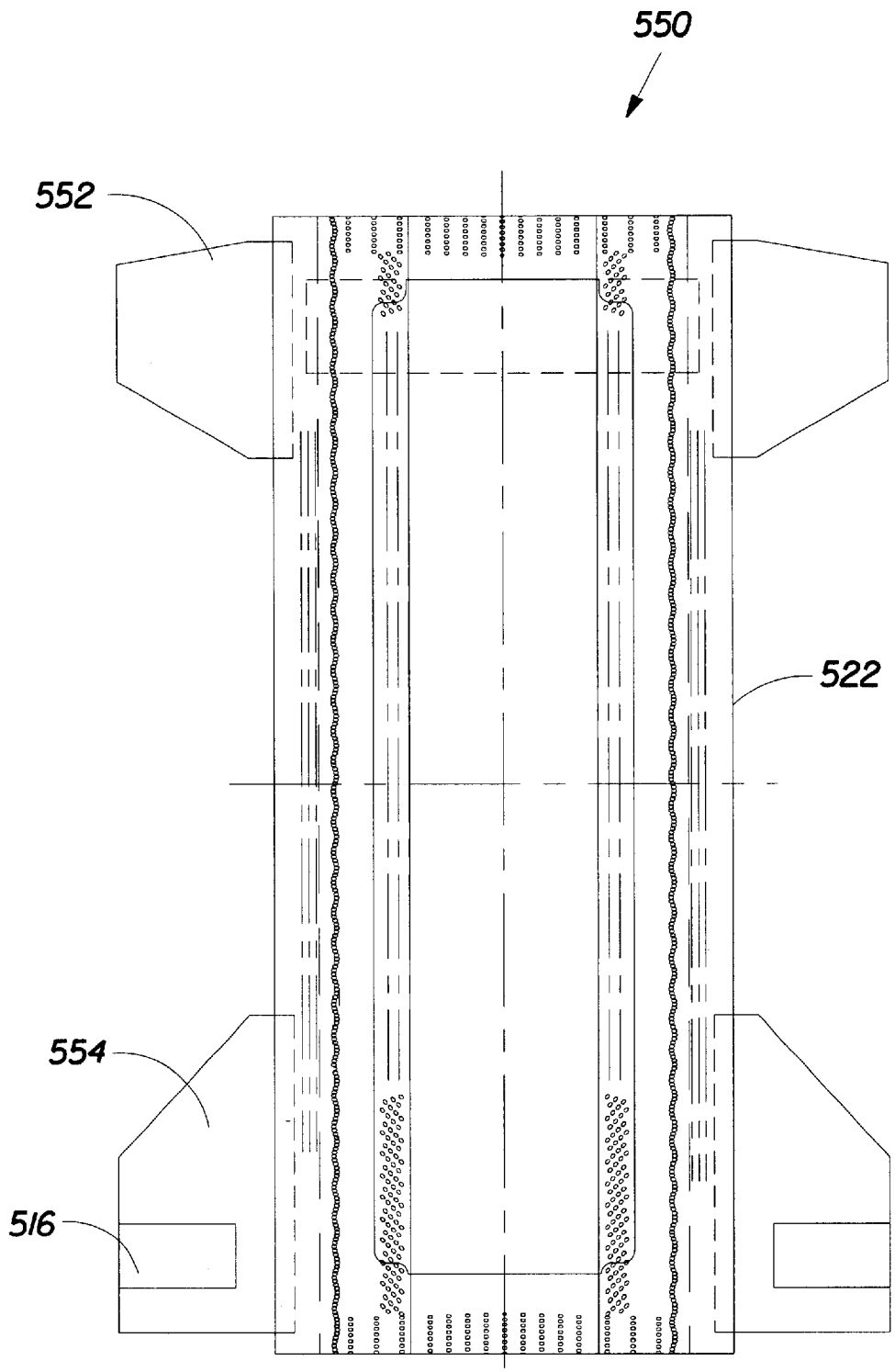
FIG. 33 is a plan view of an alternative design disposable diaper which could be manufactured using the present invention.

An example of a multi-piece disposable diaper 550 is shown in FIG. 33. The diaper 550 includes new features such as front ears 552 and back ears 554. The front ears 552 may be constructed from any single or more than one stock materials and may be joined to the chassis 502 by any means known in the art, including, but not limited to those means recited above. The back ears 554 may be elastic or extensible to provide a more comfortable and contouring fit. The back ears 554 may be constructed in various configurations. Examples of diapers with elasticized ears (or also known as side panels) are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

Figure 34:
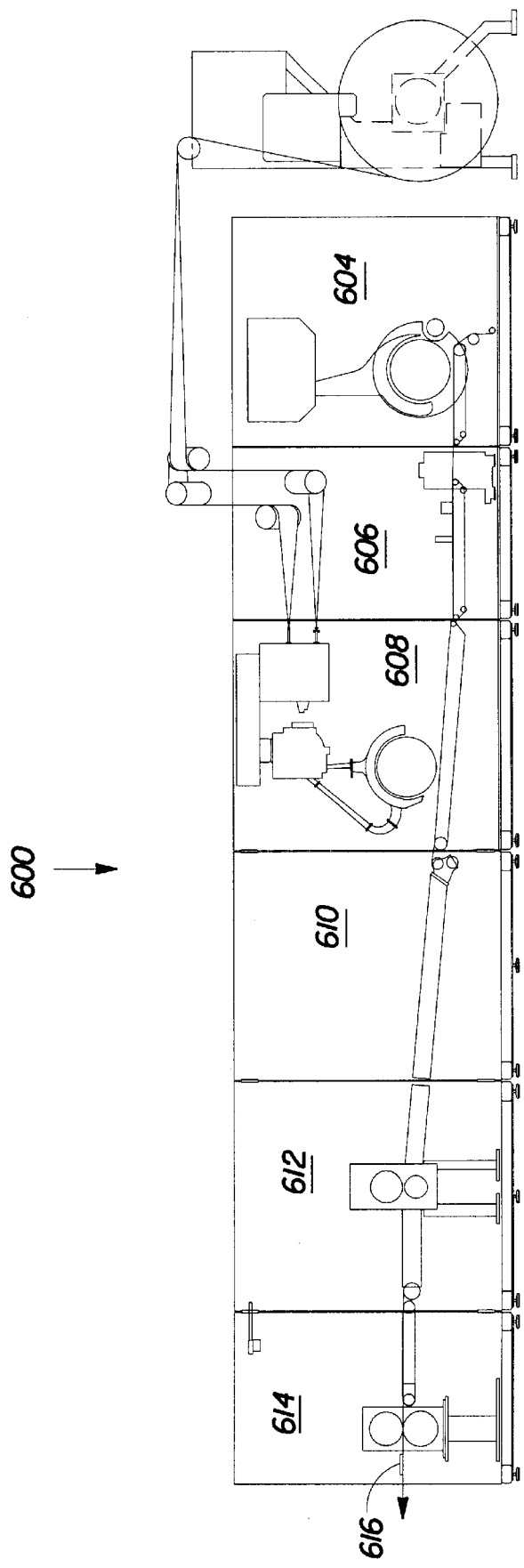
FIG. 34 is a simplified front view from the operator side of a modular absorbent core making operation which could be used for manufacturing absorbent disposable products.

An exemplary modular diaper line for making the diaper 500 shown in FIG. 32 is illustrated schematically in FIGS. 34, 35 and 37. The line may comprise fifteen modules and include an absorbent core making operation 600 shown in FIG. 34 and a converting operation 602 shown in FIGS. 35 and 37. In this embodiment, the absorbent core making operation 600 comprises six modules: a patch module 604; a tissue module 606; a dry lap module 608; a core folding module 610; a core calendar module 612; and a core cutting module 614. The individual core pads 616 formed in the absorbent core making operation 600 may be fed into converting operation 602. The converting operation 602 comprises nine modules as shown in FIGS. 35 and 37: a cuff module 620; a chassis combining in-feed module 622; a chassis combining module 624; a side panel module 626; a landing zone module 60; a fastening tape module 630; a side notch module 632; a folding module 634; and a final forming module 636.

The module 60 illustrated in FIGS. 7–10, for example, contains the following operational units attached to the front of the vertical plates 10 and 12: two unwinds 62 and 64 for unwinding a landing zone material 66; two omega rolls 68 and 70 for metering the landing zone source material 66; an automatic splicer 72 for splicing the landing zone material 66; a dancer 74 for maintaining generally equal tension in the landing zone material 66; an omega roll 76 for feeding the landing zone material 66; a tracking device 78; an adhesive applicator 80 for applying adhesive on the landing zone material 66; an idler 82 and a turning bar 84 directing a backsheet material 86; an omega roll 85 for metering the backsheet material 86; and a tracking device 88 for tracking the backsheet material 86 into a cutting device 90. The cutting device 90 may cut landing zone source material 66 and apply it onto a backsheet material 86 that may be fed from a reel 92 located on a side of the landing zone module 60 as shown in FIG. 37. In addition, the module 60 may contain a conveyor 94 for conveying a combined material 96 that passes through the module 60 from the upstream operations to the downstream operations on the production line (from right to left in FIG. 7).

FIG. 13 shows a control arrangement for the portion of the exemplary line shown in FIG. 35 in which single modules or groups of modules are individually controlled by local controllers that may be housed in standard main control panels, standard auxiliary control panels and/or standard adhesive control panels located on the panel support structure 240. The cuff module 620, for example, is designated as group A and may be controlled by a local controller housed in standard main control panel 371A and standard adhesive control panel 960A. The chassis combining group of modules B includes the chassis combining in-feed module 622 and the chassis combining module 624. The chassis combining group of modules B may be commonly controlled be a local controller housed in standard main control panel 371B and standard adhesive control panel 960B. The side panel module 626 is designated as group C and may be controlled by a local controller housed in standard main control panel 371C and standard adhesive control panel 960C. The landing zone module 60 is designated as group D and may be controlled by a local controller housed in standard main control panel 371D and standard adhesive control panel 960D. The fastening group E includes the primary fastening module 630 and the secondary fastening module 632 and may be commonly controlled be a local controller housed in standard main control panel 371E, standard auxiliary control panel 374E and standard adhesive control panel 960E. The folding module 634 and the final forming module 636 together comprise the fold and form group of modules F and may be commonly controlled be a local controller housed in standard main control panel 371F and standard auxiliary control panel 374F.

Figure 39:
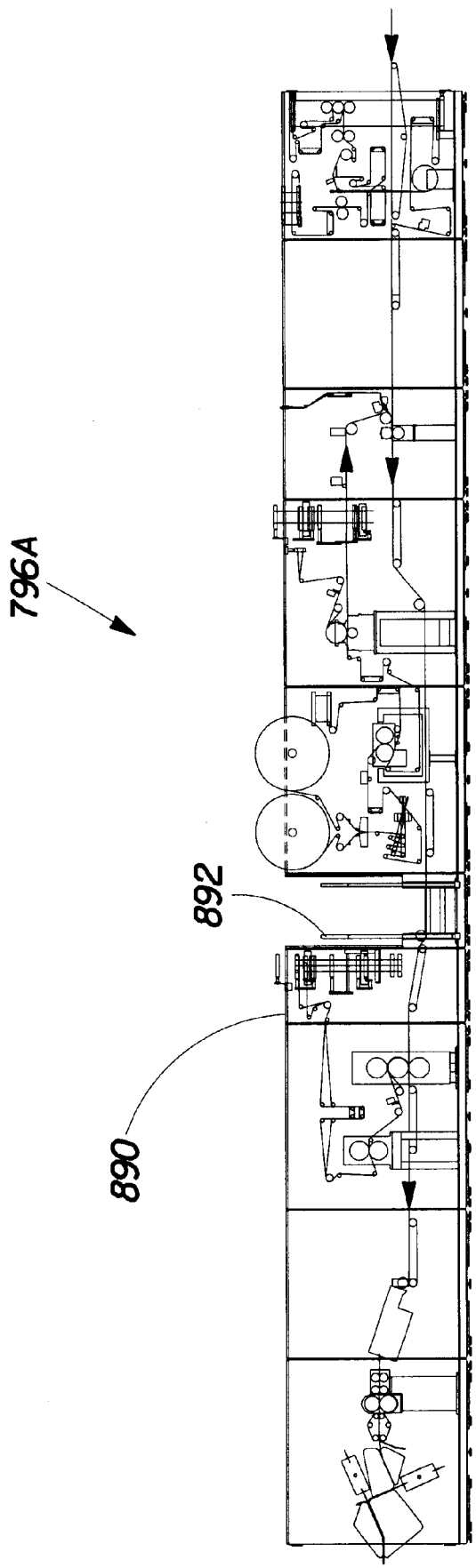
FIG. 39 is a simplified front view from the operator side of a modular converting operation shown in FIG. 36 including a cross-over module.

In another example shown in FIG. 39, a module can be used as a cross-over module 892 to create a cross-over path between both sides of the converting line 796A. In this example the back ear in-feed module 802 of the converting line 796 shown in FIG. 36 is replaced by another back ear in-feed module 890 and a cross-over module 892.

A flexible manufacturing system of the present invention may also allow for a line change that may be accomplished quickly and without expensive down time. In order to produce a multi-piece diaper 550 such as the one shown in FIG. 33, for example, the converting portion 602 shown in FIGS. 35 and 37 may be changed by removing three modules 626, 630 and 632 and inserting new modules 800, 802 and 804 shown in FIGS. 36 and 38. Specifically, the side panel module 626 may be replaced by a front ear module 800; and the fastening group of modules E, the tape module 630 and the side notch module 632, may be replaced by the back ear group of modules I, the back ear in-feed module 802 and the back ear application module 804, respectively. The standard control panels 371C and/or 960C may be reconfigured to operate as a local controller for new front ear module 800, or the standard control panels 371C and/or 960C may be replaced by control panel(s) that house a local controller for the new module 800. The standard control panels 371E, 374E and/or 960E may be reconfigured to operate as a local controller for new group of modules I, or the standard control panels 371E, 374E and/or 960E may be replaced by control panel(s) that house a local controller for the new group of modules I. A method for changing modules on a production line is described below.

The flexible manufacturing system of the present invention also allows for product upgrades to be achieved by adding, replacing or removing one or more modules to or from the flexible manufacturing system. An exemplary product upgrade of a manufacturing line such as the one shown in FIGS. 36 and 38 may include changing a multiple-layer back ear 854 of the diaper shown in FIG. 33 so that it is extensible. In this example, the back ear 854 may be made extensible such as described in U.S. Pat. No. 5,151,092 entitled "Absorbent Article With Dynamic Elastic Waist Feature Having a Predisposed Resilient Flexural Hinge" issued to Kenneth B. Buell et al. on Sep. 29, 1992, and U.S. Pat. No. 5,518,801 entitled "Web Materials Exhibiting Elastic-Like Behavior" issued to Charles W. Chappell et al. on May 21, 1996, each of which is incorporated by reference. In the manufacturing line shown in FIGS. 36 and 38, for example, the back ear in-feed module 802 or the back ear applicator module 804, which together form the back ear group of modules I, may be modified to include operational units that make the back ear 854 of the diaper 550 extensible. The new back ear 854 may be tested off-line in a standalone mode. For example, the back ear in-feed module 802 and the back ear application module 804 may be provided with an unwind device 904 and a rewind device 906. The unwind device 904 may provide a web material 908 from a reel 910 of the web 908 onto which the back ears 554, as shown in FIG. 33, produced by the modules 802 and 804 from the back ear material 854 may be applied to produce a combined web 912. When the operational units and the local controller of the back ear group I have been sufficiently tested, modified and adjusted so that the back ear group I is assembling acceptable back ears and is applying the back ears to a web in a satisfactory manner, the existing back ear in-feed module 802 in the manufacturing line may be replaced by the new back ear in-feed module that provides an extensible back ear to the back ear application module 804.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A standalone manufacturing system capable of integration into a flexible manufacturing line, the standalone manufacturing system comprising:
   a) at least one module,
   b) a first operational unit mounted to said at least one module, and c) a local controller operatively connected to said first operational unit, said local controller being adapted to control said first operational unit, to receive a virtual reference velocity and/or position signal from the flexible manufacturing line when said at least one module is connected to the flexible manufacturing line and to synchronize said first operational unit to the flexible manufacturing line based upon said virtual reference signal when said at least one module is connected to the flexible manufacturing line wherein said standalone manufacturing system is capable of a standalone mode operation by a docking station providing power distribution, safety systems, compressed air, vacuum, glycol, and adhesives, the standalone manufacturing system capable of a standalone operation, the standalone manufacturing system further includes a web material provided by an unwind stand for processing at the standalone manufacturing system, the processed web material is subsequently collected by a rewind stand, and wherein said standalone manufacturing system is capable of integration into the flexible manufacturing line by a master motion/drive reference capable of providing the virtual reference signal for synchronizing the operation of the standalone manufacturing system with the flexible manufacturing line.

2. The standalone manufacturing system of claim 1, wherein said at least one module includes a frame that is capable of supporting a second operational unit and of being moved as a unitary apparatus.

3. The standalone manufacturing system of claim 2, further comprising a plate attached to said frame, said first operational unit being attached to said plate.

4. The standalone manufacturing system of claim 1, further comprising a second operational unit mounted to said at least one module, said local controller being adapted to control said second operational unit, and to synchronize said second operational unit to the flexible manufacturing line based upon said virtual reference signal when said at least one module is connected to the flexible manufacturing line.

5. The standalone manufacturing system of claim 1, further comprising a second module attached to said at least one module, said second module including at least one second operational unit mounted to said second module, said second operational unit being operatively connected to said local controller, said local controller being adapted to control said second operational unit and to synchronize said second operational unit to the flexible manufacturing line based upon said virtual reference signal when said at least one module and said second module are connected to the flexible manufacturing line, said at least one module, said second module and said local controller together being capable of standalone operation.

6. The standalone manufacturing system of claim 1, further comprising at least one lifting mechanism mounted to said at least one module.

7. The standalone manufacturing system of claim 6, wherein said lifting mechanism is capable of floating said at least one module on a cushion of fluid.

* * * * *